US006830902B1

(12) United States Patent
Astatke et al.

(10) Patent No.: US 6,830,902 B1
(45) Date of Patent: Dec. 14, 2004

(54) COMPOSITIONS AND METHODS FOR ENHANCED SENSITIVITY AND SPECIFICITY OF NUCLEIC ACID SYNTHESIS

(75) Inventors: Mekbib Astatke, Gaithersburg, MD (US); Deb K. Chatterjee, North Potomac, MD (US); Gary F. Gerard, Frederick, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/608,066

(22) Filed: Jun. 30, 2000

Related U.S. Application Data

(60) Provisional application No. 60/142,072, filed on Jul. 2, 1999.

(51) Int. Cl.$^7$ .......................... C12P 19/34; G01N 33/53
(52) U.S. Cl. ........................................ 435/91.1; 435/7.1
(58) Field of Search .......................... 435/6, 91.2, 194, 435/810, 320.1, 91.1, 7.1; 536/22.1, 25.4, 24.3, 23.4; 935/77, 78; 530/350

(56) References Cited

U.S. PATENT DOCUMENTS

| | | | |
|---|---|---|---|
| 4,358,535 A | 11/1982 | Falkow et al. .................. | 435/5 |
| 4,446,237 A | 5/1984 | Berninger .................... | 436/504 |
| 4,563,417 A | 1/1986 | Albarella et al. .............. | 435/6 |
| 4,581,333 A | 4/1986 | Kourilsky et al. .............. | 435/6 |
| 4,582,788 A | 4/1986 | Erlich .......................... | 435/6 |
| 4,582,789 A | 4/1986 | Sheldon, III et al. ........... | 435/6 |
| 4,683,194 A | 7/1987 | Saiki et al. .................... | 435/6 |
| 4,683,202 A | 7/1987 | Mullis ......................... | 435/91 |
| 4,889,818 A | 12/1989 | Gelfand et al. .............. | 435/194 |
| 4,943,531 A * | 7/1990 | Goff et al. | |
| 4,965,188 A | 10/1990 | Mullis et al. .................... | 435/6 |
| 5,047,342 A | 9/1991 | Chatterjee ................... | 435/194 |
| 5,079,352 A | 1/1992 | Gelfand et al. ................ | 536/27 |
| 5,137,814 A | 8/1992 | Rashtchian et al. ........... | 435/91 |
| 5,143,854 A | 9/1992 | Pirrung et al. .............. | 436/518 |
| 5,194,370 A | 3/1993 | Berninger et al. .......... | 436/501 |
| 5,244,797 A | 9/1993 | Kotewicz et al. ........... | 435/194 |
| 5,252,743 A | 10/1993 | Barrett et al. ............. | 548/303.7 |
| 5,270,179 A | 12/1993 | Chatterjee .................. | 435/69.1 |
| 5,334,515 A | 8/1994 | Rashtchian et al. ........ | 435/91.2 |
| 5,338,671 A | 8/1994 | Scalice et al. .............. | 435/91.2 |
| 5,348,853 A | 9/1994 | Wang et al. .................... | 435/6 |
| 5,374,553 A | 12/1994 | Gelfand et al. .......... | 435/252.3 |
| 5,436,149 A | 7/1995 | Barnes ....................... | 435/194 |
| 5,436,327 A | 7/1995 | Southern et al. ......... | 536/25.34 |
| 5,445,934 A | 8/1995 | Fodor et al. .................... | 435/6 |
| 5,449,603 A | 9/1995 | Nielson et al. ................ | 435/6 |
| 5,455,166 A | 10/1995 | Walker ...................... | 435/91.2 |

(List continued on next page.)

FOREIGN PATENT DOCUMENTS

| | | |
|---|---|---|
| EP | 0 050 424 | 9/1981 |
| EP | 0 084 796 | 1/1983 |
| EP | 0 119 448 | 2/1984 |
| EP | 0 144 914 | 11/1984 |
| EP | 0 201 184 | 3/1986 |
| EP | 0 237 362 | 3/1987 |
| EP | 0 258 017 | 8/1987 |
| EP | 0 329 822 | 8/1988 |
| EP | 0 684 315 | 3/1995 |
| EP | 0 436 644 B1 | 4/1996 |
| EP | 0 795 612 A2 | 9/1997 |
| EP | 0 795 612 A3 | 3/1999 |
| WO | WO 88/10315 | 12/1988 |
| WO | WO 89/06700 | 7/1989 |
| WO | WO 90/03446 | 4/1990 |
| WO | WO 92/06188 | 4/1992 |
| WO | WO 92/06200 | 4/1992 |
| WO | WO 92/14845 | 9/1992 |
| WO | WO 96/10640 | 4/1996 |
| WO | WO 96/41010 | 12/1996 |
| WO | WO 98/09451 | 3/1998 |
| WO | WO 98/35060 | 8/1998 |
| WO | WO 98/47921 | 10/1998 |
| WO | WO 99/10366 | 3/1999 |

OTHER PUBLICATIONS

Abe, T. et al., "Specific inhibition of influenza virus RNA polymerase and nucleoprotein gene exppression by circular dumbbell RNA/DNA chimeric oligonucleotides containing antisense phosphodiester oligonucleotides," *FEBS Lett.* 425:91–96 (1988).

Antao, V.P. and Tinoco, I., Jr., "Thermodynamic parameters for loop formation in RNA and DNA hairpin tetraloops," *Nucl. Acids Res.* 20:819–824 (1992).

Austermann, S., et al., "Inhibition of Human Immunodeficiency Virus Type 1 Reverse Transcriptase by 3′–Blocked Oligonucleotide Primers," *Biochem. Pharmacol.* 43:2581–2589 (1992).

(List continued on next page.)

*Primary Examiner*—Kenneth R. Horlick
(74) *Attorney, Agent, or Firm*—Sterne, Kessler, Goldstein & Fox, P.L.L.C.

(57) ABSTRACT

The present invention relates to nucleic acid inhibitors, compositions and method for enhancing synthesis of nucleic acid molecules. In a preferred aspect, the invention relates to inhibition or control of nucleic acid synthesis, sequencing or amplification. Specifically, the present invention discloses nucleic acids having affinity for polypeptides with polymerase activity for use in such synthesis, amplification or sequencing reactions. The nucleic acid inhibitors are capable of inhibiting nonspecific nucleic acid synthesis under certain conditions (e.g., at ambient temperatures). Thus, in a preferred aspect, the invention relates to "hot start" synthesis of nucleic acid molecules. Accordingly, the invention prevents, reduces or substantially reduces nonspecific nucleic acid synthesis. The invention also relates to kits for synthesizing, amplifying, reverse transcribing or sequencing nucleic acid molecules comprising one or more of the nucleic acid inhibitors or compositions of the invention. The invention also relates to using the inhibitors of the invention to prevent viral replication or treat viral infections in a subject. Thus, the invention relates to therapeutic methods and pharmaceutical compositions using the inhibitors of the invention. The invention thus may be used for in vivo and in vitro inhibition of nucleic acid synthesis and/or inhibition of polymerase activity.

2 Claims, 10 Drawing Sheets

U.S. PATENT DOCUMENTS

| | | | |
|---|---|---|---|
| 5,512,462 A | 4/1996 | Cheng | 435/91.2 |
| 5,529,756 A | 6/1996 | Brennan | 422/131 |
| 5,578,467 A | 11/1996 | Schuster et al. | 435/91.2 |
| 5,587,287 A | 12/1996 | Scalice et al. | 435/6 |
| 5,593,840 A | 1/1997 | Bhatnagar et al. | 435/6 |
| 5,594,138 A | 1/1997 | Dykstra et al. | 540/596 |
| 5,594,183 A | 1/1997 | Colin | 73/864.52 |
| 5,595,890 A | 1/1997 | Newton et al. | 435/91.2 |
| 5,599,695 A | 2/1997 | Pease et al. | 435/91.1 |
| 5,605,824 A | 2/1997 | Nielson et al. | 435/194 |
| 5,614,365 A | 3/1997 | Tabor et al. | 435/6 |
| 5,639,611 A | 6/1997 | Wallace et al. | 435/6 |
| 5,646,019 A | 7/1997 | Nielson et al. | 435/91.5 |
| 5,668,005 A | 9/1997 | Kotewicz et al. | 435/194 |
| 5,693,502 A | 12/1997 | Gold et al. | 435/91.2 |
| 5,728,526 A | 3/1998 | George, Jr. et al. | 435/6 |
| 5,760,012 A | 6/1998 | Kmiec et al. | 514/44 |
| 5,763,170 A | 6/1998 | Raybuck | 435/6 |
| 5,763,173 A | 6/1998 | Gold et al. | 435/6 |
| 5,773,257 A | 6/1998 | Nielson et al. | 435/91.1 |
| 5,800,992 A | 9/1998 | Fodor et al. | 435/6 |
| 5,837,832 A | 11/1998 | Chee et al. | 536/22.1 |
| 5,846,729 A | 12/1998 | Wu et al. | 435/6 |
| 5,866,336 A | 2/1999 | Nazarenko et al. | 435/6 |
| 5,869,251 A | 2/1999 | Schuster et al. | 435/6 |
| 5,874,557 A | 2/1999 | Gold et al. | 536/23.1 |
| 5,876,930 A | 3/1999 | Livak et al. | 435/6 |
| 5,925,517 A | 7/1999 | Tyagi et al. | 435/6 |
| 5,948,899 A | 9/1999 | Arnold, Jr. et al. | 536/24.3 |
| 5,952,172 A | 9/1999 | Mende et al. | 435/6 |
| 6,020,130 A * | 2/2000 | Gold et al. | 435/6 |
| 6,037,130 A | 3/2000 | Tyagi et al. | 435/6 |
| 6,048,690 A | 4/2000 | Heller et al. | 435/6 |
| 6,090,552 A | 7/2000 | Nazarenko et al. | 435/6 |
| 6,117,634 A * | 9/2000 | Langmore et al. | 435/6 |

OTHER PUBLICATIONS

Barnes, W.M., "The Fidelity of Taq polymerase catalyzing PCR is improved by an N-terminal deletion," *Gene* 112:29–35 (1992).

Bonnett, G., et al., "Thermodynamic basis of the enhanced specificity of structured DNA probes," *Proc. Natl. Acad. Sci. USA* 96:6171–6176 (May 1999).

Cardullo et al., "Detection of nucleic acid hybridization by non radiative fluorescence resonance energy transfer," *Proc. Natl. Acad. Sci. USA* 85:8790–8794 (1988).

Chedin, F., et al., "Novel homologs of replication protein A in archaea: Implications for the evolution of ssDNA–binding proteins," *TIBS* 23:273–277 (August 1988).

Clegg, R. M., et al., "Fluorescence Resonance Energy Transfer Analysis of the Structure of the Four–Way DNA Junction," *Biochem.* 31:4846–4856 (1992).

Clegg, R.M., "Fluorescence Resonance Energy Transfer and Nucleic Acids," *Methods Enzymol.* 211:353–388 (1992).

Clegg, R.M., et al., "Observing the helical geometry of double–stranded DNA in solution by fluorescence resonance energy transfer," *Proc. Natl. Acad. Sci. USA* 90:2994–2998 (1993).

Flaman, J.–M., et al., "A rapid PCR fidelity assay," *Nucl. Acids Res.* 22:3259–3260 (1994).

Gerard, G.F., et al., "cDNA Synthesis by Moloney Murine Leukemia Virus Rnase H–Minus Reverse Transcriptase Possessing Full DNA Polymerase Activity," *FOCUS* 14:91–93 (1992).

Goodchild, J., et al., "Inhibition of human immunodeficiency virus replication by antisense oligodeoxynucleotides," *Proc. Natl. Acad. Sci. USA* 85:5507–5511 (1988).

Goodchild, J., et al., "Enhancement of ribozyme catalytic activity by a contiguous oligodeoxynucleotide (facilitator) and by 2'–o–methylation," *Nucl. Acids Res.* 20:4607–4612 (1992).

Holland, P.M., et al., "Detection of specific polymerase chain reaction product by utilizing the 5'→3' exonuclease activity of *Thermus aquaticus* DNA polymerase," *Proc. Natl. Acad. Sci. USA* 88:7276–7280 (1991).

Houts, G.E., et al., "Reverse Transcriptase from Avian Myeloblastosis Virus," *J. Virol.* 29:517–522 (1979).

Idriss, H., and Stammers, D.K., "Inhibition of HIV–1 Reverse Transcriptase by Defined Template/Primer DNA Oligonucleotides: Effect of Template Length and Binding Characteristics," *J. Enzyme Inhib.* 8:91–112 (1994).

Jendis, J., et al., "Inhibition of Replication of Fresh HIV Type 1 Pateint Isolates by a Polypruine Tract–Specific Self–Complementary Oligodeoxynucleotide," *AIDS Res. Human Retrov.* 12:1161–1168 (1996).

Ju, J., et al., "Fluorescence energy transfer dye–labeled primers of DNA sequencing and analysis," *Proc. Natl. Acad. Sci. USA* 92:4347–4351 (1995).

Kainz, A.P., et al., "Specifically–Enhanced Hot–Start PCR: Addition of Double–Stranded DNA Fragments Adapted to the Annealing Temperature," *BioTechniques* 28:278–282 (Feb. 2000).

Kelly, T.J., et al., "Identification and characterization of a single–stranded DNA–binding protein from the archeon *Methanococcus jannaschii*," *Proc. Natl. Acad. Sci. USA* 95:14634–14639 (1989).

Kinchington, D., et al., "A comparison of gag, pol and rev antisense oligonucleotides as inhibitors of HIV–1," *Antiviral Res.* 17:53–62 (1992).

Kleppe, K., et al., "Studies on Polynucleotides, XCVI. Repair Replications of Short Synthetic DNA's as Catalyzed by DNA Polymerases," *J. Mol. Biol.* 56:341–361 (1971).

Kotewicz, M.L., et al., "Isolation of cloned moloney murine leukemia virus rReverse tTranscriptase lacking ribonuclease H activity," *Nucl. Acids Res.* 16:265–277 (1988).

Koga, M., et al., "Alternating α, β–Oligothymidylates with Alternating (3'→3")–and (5'→5")–Internucleotidic Phosphodiester Linkages as Models for Antisense Oligodeoxyribonucleotides," *J. Organ. Chem.* 56:3757–3759 (1991).

Kuwaski, T., et al., "Hairpin Antisense Oligonucleotide Containing 2'–Methoxynucleosides with Base–Pairing in the Stem Region at the 3'–end: Penetration, Localization, and Anti–HIV Activity," *Biochem. Biophys. Res.* 229:623–631 (1996).

Kwoh, D.Y., et al., "Transcription–based aplification system and detection of amplified human immunodeficiency virus type 1 with a bead–based sandwich hybridization format," *Proc. Natl. Acad. Sci. USA* 86:1173–1177 (1989).

Lawyer, F.C., et al., "High–Level Expression Purification, and Enzymatic Characterization of Full–Length *Thermus aquaticus* DNA Polymerase and a Truncated Form Deficient in 5' to 3' Exonuclease Activity," *PCR Meth. Appl.* 2:275–287 (1993).

Lee, L.G., et al., "Allelic discrimination by nick–translation PCR with fluorogenic probes," *Nucl. Acids Res.* 21:3761–3766 (1993).

Luo, G., et al., "Inhibition of influenza viral polymerases by minimal viral RNA decoys," *J. Gen. Virol.* 78:2329–2333 (1997).

Lyamichev, V., et al., "Structure–Specific Endonucleolytic Cleavage of Nucleic Acids by Eubacterial DNA Polymerases," *Science* 260:778–783 (1993).

Maury, G., et al., "Template. Phosphorothioate Oligonucleotides Duplexes as Inhibitors of HIV–1 Reverse Transcriptase," *Biochem. Biophys. Res. Coomun.* 186:1249–1256 (1992).

Matsukura, M., "Regulation of viral expression of human immunodefficiency virus in vitro by an antisense phosphorothioate oligonucleotide against Rev (Art/Trs) in chronically infected cells," *Proc. Natl. Acad. Sci. USA* 86:4244–4248 (1989).

Mullis, K., et al., "Specific Enzymatic Amplification of DNA in Vitro: The Polymerase Chain Reaction," *Cold Spring Harbor Symp. Quant. Biol.* 51:263–273 (1986).

Nakaya, T., et al., "Decoy Approach Using RNA–DNA Chimera Oligonucleotides to Inhibit the Regulatory Function of Human Immunodeficiency Virus Type 1 Rev Protein," *Antimicro. Agents Chemother.* 41:319–325 (1997).

Nazarenko, I.A., et al., "A closed tube format for amplification and detection of DNA based on energy transfer," *Nucl. Acids Res.* 25:2516–2521 (1997).

Ozaki, H., and McLaughlin, L.W., "The estimation of distances between specific backbone–labeled sites in DNA using fluorescence resonance energy transfer," *Nucl. Acids Res.* 20:5205–5214 (1992).

Panet, A., and Khorana, H.G., "Studies on Polynucleotides. The Linkage of Deoxyribopolynucleotide Templates to Cellulose and its Use in Their Replication," *J. Biol. Chem.* 249:5214–5221 (1974).

Paris, P.L., et al., "Probing DNA sequences in solution with a monomer–excimer fluorescene color change,"*Nucl. Acids Res.* 26:3789–3793 (1998).

Rossi, J.J., et al., "Ribozymes as Anti–HIV–1 Therapeutic Agents: Principles, Applications, and Problems," *AIDS Res. Human Retro.* 8:183–189 (1992).

Saiki, R.K., et al., "Primer–Directed Enzymatic Amplification of DNA with a Thermostable DNA Polymerase," *Science* 239:487–491 (1988).

Sarin, P.S., et al., "Inhibition of acquired immunodeficiency syndrome virus by oligodeoxynucleoside methylphosphonates," *Proc. Natl. Acad. Sci. USA* 85:7448–7451 (1988).

Schneider, D.J., et al., "High Affinity ssDNA Inhibitors of the Reverse Transcriptase of Type 1 Human Immunodeficiency Virus," *Biochem.* 34:9599–9610 (1995).

Selvin, P.R., "Fluorescence Resonance Energy Transfer," *Methods Enzymol.* 246:300–334 (1995).

Selvin, P.R., and Hearst, J.E., "Luminescence energy transfer using a terbium chelate: Improvements on fluorescence energy transfer," *Proc. Natl. Acad. Sci USA* 91:10024–10028 (1994).

Soltis, D.A., and Skalka, A.M., "The α and β chains of avian retrovirus reverse transcriptase independently expressed in *Escherichia coli:* characterization of enzymatic activities," *Proc. Natl. Acad. Sci. USA* 85:3372–3376 (1988).

Stein, C.A., et al., "Physicochemical properties of phosphorothioate oligodeoxynucleotides," *Nucl. Acids Res.* 16:3209–3221 (1988).

Tabor, S., and Richardson, C.C., "A single residue in DNA polymerase of the *Escherichia coli* DNA polymerase I family is critical for distinguishing between deoxy–and dideoxyribonucleotides," *Proc. Natl. Acad. Sci. USA* 92:6339–6343 (1995).

Tyagi, S., and Kramer, F.R., "Molecular Beacons: Probes that Fluoresce Upon Hybridization," *Nature Biotechnol.* 14:303–309 (1996).

Wang, Y., et al., "Rapid Sizing of Short Tandem Repeat Alleles Using Capillary Array Electrophoresis and Energy–Transfer Fluorescent Primers," *Anal. Chem.* 67:1197–1203 (1995).

Wu, D.Y., et al., "Allele–specific enzymatic amplification of β–globin genomic DNA for diagnosis of sickle cell anemia," *Proc. Natl. Acad. Sci., USA,* 86:2757–2760 (1989).

Wu, D.Y., et al., "The Ligation Amplification Reaction (LAR)–Amplification of Specific DNA Sequences Using Sequential Rounds of Template–Dependent Ligation," *Genomics* 4:560–569 (1989).

Xu, D., et al., "Melting and Premelting Transitions of an Oligomer Measured by DNA Base Fluorescence and Absorption," *Biochem.* 33:9592–9599 (1994).

Yamana, K, et al., "Fluorescent–labeled Oligonucleotides that Exhibit a Measurable Signal in the Presence of Complementary DNA," *Nucl. Acids Symp. Ser.* 27:135–136 (1992).

"Amplifluor™ Universal Amplification & Detection System," Intergen Company Catalog, 4 pp., (1999).

Ailenberg, M., and Silverman, M., "Controlled Hot Start and Improved Specificity in Carrying Out PCR Utilizing Touch–Up and Loop Incorporated Primers (TULIPS)," *BioTechniques* 29:1018–1024, Eaton Publishing Company, Natick, Mass. (Nov. 2000).

Austermann, S., et al., "Inhibition of Human Immunodeficiency Virus Type 1 Reverse Transcriptase by 3'–Blocked Oligonucleotide Primers," *Biochem. Pharmacol.* 43:2581–2589, Elsevier Science, Oxford, England (1992).

Lin, Y. and Jayasena, S.D., "Inhibition of Multiple Thermostable DNA Polymerases by a Heterodimeric Aptamer," *J. Mol. Biol.* 271:100–111, Academic Press, Inc., New York, N.Y. (1997).

International Search Report for PCT/US00/18256, mailed Nov. 7, 2000.

Idriss, H., and Stammers, D.K., "Inhibition of HIV–1 Reserve Transcriptase by Defined Template/Primer DNA Oligonucleotides: Effect of Template Length and Binding Characteristis," *J. Enzyme Inhib.* 8:97–112, Harwood Academic Publishers GmbH (1994).

Kaboev, O.K., et al., "PCR hot start using primers with the structure of molecular beacons (hairpin–like structures)," *Nucl. Acids Res.* 28:e94, Oxford University Press, Oxford, England (Nov. 2000).

Kuwasaki, T., et al., "Hairpin Antisense Oligonucleotides Containing 2'–Methoxynucleosides with Base–Pairing in the Stem Region at the 3'–end: Penetration, Localization and Anti–HIV Activity," *Biochem. Biophys. Res. Commun.* 228:623–631, Academic Press, Inc., Orlando, Fla. (1996).

\* cited by examiner

COMPOSITIONS AND METHODS FOR ENHANCED SENSITIVITY AND SPECIFICITY OF NUCLEIC ACID SYNTHESIS

CROSS-REFERENCE TO RELATED APPLICATIONS

This application is related to U.S. provisional patent application No. 60/142,072 filed Jul. 2, 1999, which is specifically incorporated herein in its entirety.

FIELD OF THE INVENTION

The present invention relates to a method for increasing sensitivity and specificity of nucleic acid synthesis by reducing nonspecific nucleic acid synthesis occurring at ambient temperature. The invention also relates to novel nucleic acids which have high affinity to polymerases. The methods and compositions of the present invention can be used in DNA sequencing, amplification reactions, nucleic acid synthesis and cDNA synthesis.

The invention also relates to nucleic acids and compositions which are capable of inhibiting or preventing nucleic acid synthesis, sequencing, amplification and cDNA synthesis, for example, by binding one or more polypeptides with polymerase activity. In addition, the materials and methods of the present invention may be used as therapeutics to inhibit the replication of organisms that rely upon a reverse transcriptase activity for completion of their life cycle, such as retroviruses. The invention also relates to vectors and host cells comprising such nucleic acid molecules. The invention also concerns kits comprising the compositions or nucleic acids of the invention.

BACKGROUND OF THE INVENTION

DNA polymerases synthesize the formation of DNA molecules which are complementary to a DNA template. Upon hybridization of a primer to the single-stranded DNA template, polymerases synthesize DNA in the 5' to 3' direction, successively adding nucleotides to the 3'-hydroxyl group of the growing strand. Thus, in the presence of deoxyribonucleoside triphosphates (dNTPs) and a primer, a new DNA molecule, complementary to the single stranded DNA template, can be synthesized.

Both mesophilic and thermophilic DNA polymerases are used to synthesize nucleic acids. Using thermostable rather than mesophilic polymerases is preferable since the higher annealing temperatures used with thermostable polymerases result in less non-specific DNA amplification from extension of mis-annealed primers. Even with thermostable polymerases, however, some primer sequences and certain experimental conditions can result in the synthesis of a significant amount of non-specific DNA products. These non-specific products can reduce the sensitivity of polymerase-based assays and can require extensive optimization for each primer set. In addition, this problem is intensified when polymerases having a high level of activity at ambient temperature are employed (for example, DNA polymerase from *Thermotoga neapolitana*).

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein and RNA which the gene encodes. In order to produce a protein, a complementary copy of one strand of the DNA double helix (the "coding" strand) is produced by polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist many mRNA species, each encoding a separate and specific protein. This fact provides a powerful tool to investigators interested in studying genetic expression in a tissue or cell. mRNA molecules may be isolated and further manipulated by various molecular biological techniques, thereby allowing the elucidation of the full functional genetic content of a cell, tissue or organism.

A common approach to the study of gene expression is the production of complementary DNA (cDNA) clones. In this technique, the mRNA molecules from an organism are isolated from an extract of the cells or tissues of the organism. This isolation often employs chromatography matrices, such as cellulose or agarose, to which oligomers of thymidine (T) have been complexed. Since the 3' termini on most eukaryotic mRNA molecules contain a string of Adenosine (A) bases, and since A binds to T, the mRNA molecules can be rapidly purified from other molecules and substances in the tissue or cell extract. From these purified mRNA molecules, cDNA copies may be made using the enzyme reverse transcriptase (RT) or DNA polymerases having RT activity, which results in the production of single-stranded cDNA molecules. The single-stranded cDNAs may then be converted into a complete double-stranded DNA copy (i.e., a double-stranded cDNA) of the original mRNA (and thus of the original double-stranded DNA sequences, encoding this mRNA, contained in the genome of the organism) by the action of a DNA polymerase. The protein-specific double-stranded cDNAs can then be inserted into a vector, which is then introduced into a host bacterial, yeast, animal or plant cell, a process referred to as transformation or transfection. The host cells are then grown in culture media, resulting in a population of host cells containing (or in many cases, expressing) the gene of interest or portions of the gene of interest.

This entire process, from isolation of mRNA to insertion of the cDNA into a vector (e.g., plasmid, viral vector, cosmid, etc.) to growth of host cell populations containing the isolated gene or gene portions, is termed "cDNA cloning." If cDNAs are prepared from a number of different mRNAs, the resulting set of cDNAs is called a "cDNA library," an appropriate term since the set of cDNAs represents a "population" of genes or portions of genes comprising the functional genetic information present in the source cell, tissue or organism.

Synthesis of a cDNA molecule initiates at or near the 3' termini of the mRNA molecules and proceeds in the 5'-to-3' direction successively adding nucleotides to the growing strand. Priming of the cDNA synthesis at the 3'-termini at the poly A tail using an oligo (dT) primer ensures that the 3' message of the mRNAs will be represented in the cDNA molecules produced. The ability to increase sensitivity and specificity during cDNA synthesis provides more representative cDNA libraries and may increase the likelihood of the cDNA library having full-length cDNA molecules (e.g., full-length genes). Such advances would greatly improve the probability of finding full-length genes of interest.

In addition to their importance for research purposes, reverse transcriptase enzymes play a critical role in the life cycle of many important pathogenic viruses, in particular, the human immunodeficiency viruses (HIV). In order to complete its life cycle, HIV and other similar viruses must use a reserve transcriptase enzyme to convert the viral RNA genome into DNA for integration into the host's genomic material. Since this step is critical to the viral life cycle and host cells do not have any similar requirement for reverse transcriptase activity, the reverse transcriptase enzyme has been intensively studied as a chemotherapeutic target. In general, the bulk of therapeutic reagents directed at the reverse transcriptase enzyme have been nucleotide analogues, for example AZT. Other therapeutic modalities using oligonucleotide-based reagents, e.g., anti-sense oligonucleotides and ribozymes, have been used to inhibit viral replication, however, these reagents are not targeted specifically against reverse transcriptase activity, instead of being targeted against the nucleic acid of the viral genome. See, for example, Goodchild, et al., "Inhibition of human immunodeficiency virus replication by antisense oligodeoxynucleotides," *Proc. Natl. Acad. Sci. USA* 85:5507–5511 (1988), Matsukara, et al., "Regulation of viral expression of human immunodeficiency virus in vitro by an antisense phosphorothioate oligodeoxynucleotide against rev (art/trs) in chronically infected cells," *Proc. Natl. Acad Sci. USA* 86:4244–4248 (1989), Rossi, et al., "Ribozymes as Anti-HIV-1 Therapeutic Agents: Principles, Applications, and Problems," *Aids Research and Human Retroviruses* 8:183:189 (1992), Goodchild, "Enhancement of ribozyme catalytic activity by a contiguous oligodeoxynucleotide (facilitator) and by 2'-O-methylation," *Nucleic Acids Research* 20:4607–4612 (1992) and Kinchington, et al., "A comparison of gag, pol and rev antisense oligodeoxynucleotides as inhibitors of HIV-1," *Antiviral Research* 17:53–62 (1992) which are specifically incorporated herein by reference. Oligonucleotides that have been blocked at the 3'-end to prevent their elongation by reverse transcriptase have also been considered as inhibitors (see, for example, Austermann, et al., "Inhibition of human immunodeficiency virus type 1 reverse transcriptase by 3'-blocked oligonucleotides" *Biochemical Pharmacology* 43(12):2581–2589 (1992). Each of the above cited references is specifically incorporated herein in its entirety.

Oligonucleotides have been investigated for anti-HIV activity. For example, Idriss, et al. (1994), *Journal of Enzyme Inhibition* 8(2)97–112, disclose DNA oligonucleotides in a hairpin structure as inhibitors of HIV RT activity while Kuwasaki, et al., (1996) *Biochemical and Biophysical Research Communications* 228:623–631 disclose anti-sense hairpin oligonucleotides containing a mixture of deoxy and 2'-methoxy-nucleotides with anti-HIV activity.

Notwithstanding these and other efforts to modulate the activity of polymerases, there remains a need in the art for materials and methods to prevent the undesirable activity of the polymerases while permitting the synthesis of nucleic acids by the polymerase when such synthesis is desired. These and other needs are met by the present invention.

SUMMARY OF THE INVENTION

The present invention provides materials and methods for inhibiting, reducing, substantially reducing or eliminating nucleic acid synthesis under certain conditions (preferably at ambient temperatures and/or within a cell) while permitting synthesis when such synthesis is desired.

In a preferred aspect, the invention relates to methods for the prevention or inhibition of nucleic acid synthesis during reaction set up (e.g., in vitro) and preferably before optimum reaction conditions for nucleic acid synthesis are achieved. Such inhibition of synthesis at sub-optimum conditions or during reaction set up prevents or reduces non-specific nucleic acid synthesis. Once reaction set up is complete and the optimum conditions are reached, nucleic acid synthesis can be initiated.

In another aspect, the present invention relates to a method of inhibiting a polymerase enzyme within a cell (e.g., in vivo) by introducing into the cell an oligonucleotide or inhibitor of the invention, preferably said oligonucleotide comprises a 5'- and a 3'-portion, wherein the said 3'-portion comprises one or more deoxyribonucleotides or derivatives thereof and said 5'-portion comprises one or more ribonucleotides or derivatives thereof and wherein all or a portion of said 3'-portion is capable of base pairing to all or a portion of said 5'-portion and incubating said cell under conditions causing the inhibition of the polymerase. In some embodiments, the 5'-portion of the oligonucleotide which comprises ribonucleotides forms a 5'-overhang. In another aspect, the oligonucleotide is in the form of a hairpin and preferably the stem of the hairpin comprises a series of contiguous ribonucleotides based paired or hybridized with a series of continguous deoxyribonucleotides. In some embodiments the polymerase is a reverse transcriptase and may preferably be an HIV reverse transcriptase.

In another aspect, the present invention provides a method of inhibiting replication of a virus, by providing a virus, said virus comprising a reverse transcriptase and requiring activity of the reverse transcriptase for replication and contacting said reverse transcriptase with an oligonucleotide or inhibitor of the invention that inhibits activity of said reverse transcriptase thereby inhibiting replication of said virus. In some embodiments, the oligonucleotide comprises a 5'- and a 3'-portion, wherein said 3'-portion comprises one or more deoxyribonucleotides or derivatives thereof and said 5'-portion comprises one or more ribonucleotides or derivatives thereof and wherein all or a portion of said 3'-portion is capable of base pairing to all or a portion of said 5'-portion. In some embodiments, the 5'-portion of the oligonucleotide which comprises ribonucleotides forms a 5'-overhang. In another aspect, the oligonucleotide is in the form of a hairpin and preferably the stem of the hairpin comprises a series of contiguous ribonucleotides base paired or hybridized with a series of contiguous deoxyribonucleotides. In some embodiments, the virus is an HIV. In some embodiments, contacting comprises introducing said oligonucleotide into a cell.

More specifically, the invention relates to controlling nucleic acid synthesis by introducing an inhibitory nucleic acid or oligonucleotide which binds to or interacts with the polypeptide with polymerase activity (e.g., DNA polymerases, reverse transcriptases, etc.). Accordingly, such inhibitory nucleic acids or oligonucleotide can bind the polymerase and interfere with nucleic acid synthesis by preventing binding or interaction of the polymerase or reverse transcriptase with the primer/template. Preferably, such inhibitory nucleic acid molecules are double stranded molecules although any form of nucleic acid molecule may be used as long as the molecule can bind or interact with the polymerization enzyme of interest. Such molecules may be DNA, RNA, DNA/RNA hybrids, double stranded DNA, double stranded RNA and DNA/RNA double stranded molecules. Derivative nucleic acid molecules may also be used such as Protein Nucleic Acids (PNAs), linked nucleic acids (LNA, available form Proligo, Boulder Colo.) and nucleic acid molecules comprising modified nucleotides. Moreover, the nucleic acid molecules may be in any form or topology such as linear, circular, supercoiled, double stranded with one or more single stranded portions, hairpin structure, or complexed with other molecules such as peptides or proteins and the like. Such inhibitory nucleic acids preferably include double-stranded nucleic acid molecules (which may comprise one or more internal, 5' and/or 3' single stranded portions), or single stranded nucleic acid molecules capable of folding into a double stranded form, i.e. forming one or more hairpin-loops, such that at least one double stranded portion of the nucleic acid molecule is capable of binding to a polypeptide with polymerase activity. In one aspect, the nucleic acid molecules used in the invention bind the polypeptide having polymerase activity (e.g., DNA polymerase, reverse transcriptase, etc.) with high affinity. Once the polymerase or reverse transcriptase is complexed with the inhibitory nucleic acid, it is unavailable for annealing to the primer/template substrate, resulting in reduced, substantially reduced, or no polymerase or reverse transcriptase activity. In some embodiments, the oligonucleotides of the present invention may comprise a 5'- and a 3'-portion, wherein said 3'-portion comprises one or more deoxyribonucleotides or derivatives thereof and said 5'-portion comprises one or more ribonucleotides or derivatives thereof and wherein all or a portion of said 3'-portion is capable of base pairing to all or a portion of said 5'-portion. In some embodiments, the oligonucleotides of the invention may comprise a 5'-portion, wherein said 5'-portion comprising ribonucleotides forms a 5'-overhang. In some embodiments, an oligonucleotide of the invention may comprise one or more modifications so as to be non-extendable. In some embodiments, this modification may be to the 3'-most nucleotide. In some embodiments, the modification is phosphorylation of the 3'-most nucleotide at the 3'-hydroxyl. An oligonucleotide of the present invention may comprise one or more modifications so as to be resistant to digestion or degradation by, for example, one or more nucleases. In some embodiments, this modification may be the incorporation of one or more phophorothioate moieties. In some embodiments, the modification may comprise alkylation of one or more hydroxl groups.

Thus, the inhibitory nucleic acid is preferably introduced into the reaction mixture where it competitively binds to or interacts with the polymerase, thereby inhibiting synthesis by the polymerase under particular reaction conditions. Thus, interaction or binding of the inhibitor and polymerase preferably results in the formation of an inhibitor/polymerase complex.

The inhibition of polymerase activity or nucleic acid synthesis by the nucleic acids of the invention is preferably reduced, substantially reduced, inhibited, or eliminated so that nucleic acid synthesis may proceed when reaction conditions are changed, for example, when the temperature is raised. In a preferred aspect, the changed conditions affect the ability of the inhibitory nucleic acids to interact with the polymerase causing release of the polymerase and/or denaturation or inactivation of the inhibitory nucleic acids making the polymerase available thus allowing nucleic acid synthesis to proceed. In one aspect, the inhibitory nucleic acids and the primer/template substrate competitively interact with the polymerase to prevent synthesis. Under the changed conditions, the competitive interaction is reduced such that nucleic acid synthesis occurs. In another aspect, the changed conditions cause the double stranded inhibitory nucleic acid molecule(s) (including hairpins) to denature or melt such that single stranded molecules are formed which do not substantially bind or interact with the polymerase. In another aspect, a second change in conditions (i.e., temperature is lowered to, for example, ambient temperatures) allows the inhibitor nucleic acid molecules of the invention to reactivate or again inhibit nucleic acid synthesis. That is, the inhibitors may again interact or bind with the polymerase or reverse transcriptase under the changed conditions. For example, the changed conditions may allow the inhibitor to form double stranded molecules which effectively enhances its binding or interacting capacity with the polymerase or reverse transcriptases. Thus, in accordance with the invention, the inhibitors may be reused or recycleable during synthesis reactions (single or multiple) which may require multiple adjustment or changes in reaction conditions (i.e., temperature changes), without the need to add additional inhibitor.

The invention therefore relates to a method for synthesizing one or more nucleic acid molecules, comprising (a) mixing one or more nucleic acid templates (which may be a DNA molecule such as a cDNA molecule, or an RNA molecule such as an mRNA molecule) with one or more primers, and one or more inhibitory nucleic acids or compositions of the present invention capable of binding or interacting with an enzyme having polymerase activity, and (b) incubating the mixture in the presence of one or more enzymes having nucleic acid polymerase activity (e.g., DNA polymerases or reverse transcriptases) under conditions sufficient to synthesize one or more first nucleic acid molecules complementary to all or a portion of the templates. Alternatively, the method may comprise mixing one or more inhibitor nucleic acids with one or more polymerases and incubating such mixtures under conditions sufficient to synthesize one or more nucleic acid molecules. Such conditions may involve the use of one or more nucleotides and one or more nucleic acid synthesis buffers. Such methods of the invention may optionally comprise one or more additional steps, such as incubating the synthesized first nucleic acid molecule under conditions sufficient to make a second nucleic acid molecule complementary to all or a portion of the first nucleic acid molecule. These additional steps may also comprise the use of the inhibitory nucleic acid molecules of the invention. The invention also relates to nucleic acid molecules synthesized by these methods.

In a related aspect, the nucleic acid synthesis method may comprise (a) mixing one or more polymerases with one or more of the inhibitory nucleic acid molecules of the invention, and (b) incubating such mixture under conditions sufficient to inactivate or substantially inhibit or reduce polymerase activity of such polymerases. In another aspect, such incubation is under conditions sufficient to inhibit or prevent such nucleic acid synthesis.

The invention also relates to a method for amplifying one or more nucleic acid molecules, comprising (a) mixing one or more nucleic acid templates with one or more primers, and one or more inhibitory nucleic acid molecules or compositions of the present invention capable of binding or interacting with an enzyme having polymerase activity and (b) incubating the mixture in the presence of one or more enzymes having nucleic acid polymerase activity (e.g., DNA polymerases) under conditions sufficient to amplify one or more nucleic acid molecules complementary to all or a portion of the templates. More specifically, the invention relates to a method of amplifying a DNA molecule comprising: (a) providing a first and second primer, wherein said first primer is complementary to a sequence within or at or near the 3'-termini of the first strand of said DNA molecule and said second primer is complementary to a sequence within or at or near the 3'-termini of the second strand of said DNA molecule, and one or more inhibitory nucleic acids or compositions of the invention (e.g., a nucleic acid having affinity for an enzyme with polymerase activity); (b) hybridizing said first primer to said first strand and said second primer to said second strand; (c) incubating the mixture under conditions such that a third DNA molecule complementary to all or a portion of said first strand and a fourth DNA molecule complementary to all or a portion of said second strand are synthesized; (d) denaturing said first and third strand, and said second and fourth strands; and (e) repeating steps (a) to (c) or (d) one or more times. Such conditions may include incubation in the presence of one or more polymerases, one or more nucleotides and/or one or more buffering salts. The invention also relates to nucleic acid molecules amplified by these methods.

In a related aspect, the nucleic acid amplification method may comprise (a) mixing one or more polymerases with one or more of the inhibitory nucleic acid molecules of the invention, and (b) incubating such mixture under conditions sufficient to inactivate or substantially inhibit or reduce polymerase activity of such polymerases. In another aspect, such incubation is under conditions sufficient to inhibit or prevent such nucleic acid amplification.

The invention also relates to methods for sequencing a nucleic acid molecule comprising (a) mixing a nucleic acid molecule to be sequenced with one or more primers, one or more of the inhibitory nucleic acids or compositions of the invention, one or more nucleotides and one or more terminating agents to form a mixture; (b) incubating the mixture under conditions sufficient to synthesize a population of molecules complementary to all or a portion of the molecule to be sequenced; and (c) separating the population to determine the nucleotide sequences of all or a portion of the molecule to be sequenced. The invention more specifically relates to a method of sequencing a nucleic acid molecule, comprising: (a) providing an inhibitory nucleic acid or composition of the present invention (to which an enzyme with polymerase activity as affinity), one or more nucleotides, and one or more terminating agents; (b) hybridizing a primer to a first nucleic acid molecule; (c) incubating the mixture of step (b) under conditions sufficient to synthesize a random population of nucleic acid molecules complementary to said first nucleic acid molecule, wherein said synthesized molecules are shorter in length than said first molecule and wherein said synthesized molecules comprise a terminator nucleotide at their 3' termini; and (d) separating said synthesized molecules by size so that at least a part of the nucleotide sequences of said first nucleic acid molecule can be determined. Such terminator nucleotides include dideoxyribonucleoside thiphophates such as ddNTP, ddATP, ddGTP, ddITP or ddCTP. Such conditions may include incubation in the presence of one or more polymerases and/or buffering salts.

In a related aspect, the nucleic acid sequencing method may comprise (a) mixing one or more polymerases with one or more of the inhibitory nucleic acid molecules of the invention, and (b) incubating such mixture under conditions sufficient to inactivate or substantially inhibit polymerase activity of such polymerases. In another aspect, such incubation is under conditions sufficient to inhibit or prevent such nucleic acid sequencing.

The invention also relates to the inhibitory nucleic acids of the invention and to compositions comprising the inhibitory nucleic acids of the invention, to vectors (which may be expression vectors) comprising these nucleic acid molecules, and to host cells comprising these nucleic acid molecules or vectors. Compositions of the invention may also include those compositions made for carrying out the methods of the invention or produced while carrying out such methods. The invention also relates to pharmaceutical compositions. Such compositions may comprise one or more of the inhibitory nucleic acid molecules or oligonucleotides of the invention and at least one other component selected from the group consisting of one or more nucleotides, one or more polymerases (e.g., thermophilic or mesophilic DNA polymerases and/or reverse transcriptases), one or more suitable buffers or buffer salts, one or more primers, one or more terminating agents, one or more viruses, one or more cells, and one or more amplified or synthesized nucleic acid molecules produced by the methods of the invention. The invention also relates to methods of producing an inhibitory nucleic acid comprising culturing the above-described host cells under conditions favoring the production of the nucleic acid by the host cells, and isolating the nucleic acid. The invention also relates to nucleic acid produced by synthetic methods. Such inhibitory nucleic acid molecules of the invention may also be made by standard chemical synthesis techniques.

In a related aspect, the present invention provides materials and methods for the in vivo inhibition of polymerase activity. In some embodiments, the present invention provides for the introduction of the inhibitory oligonucleotides of the present invention into an organism thereby inhibiting a polymerase present within the organism. In some embodiments, the polymerase may be a reverse transcriptase, preferably a viral reverse transcriptase. In some embodiments, the present invention provides a method for the inhibition of a viral reverse transcriptase comprising contacting a cell or virus expressing a viral reverse transcriptase with an inhibitory oligonucleotide under conditions causing the oligonucleotide to inhibit the reverse transcriptiase. Preferably, the oligonucleotide is contacted with the cell under conditions sufficient to have the oligonucleotide taken up by the cell by well known techniques. In some embodiments, the present invention provides a method of inhibiting the growth of a virus, comprising contacting a cell infected with a virus that requires reverse transcriptase activity to complete its life cycle with an inhibitory oligonucleotide under conditions causing the oligonucleotide to be taken up by the cell and causing the reverse transcriptase to be inhibited thereby inhibiting the growth of the virus. In some embodiments, the present invention provides a method of treating an organism or subject infected with a virus that requires reverse transcriptase activity to complete its life cycle comprising contacting an infected cell of the organism or subject with a composition comprising an inhibitory oligonucleotide under conditions causing the oligonucleotide to be taken up by the cell and causing the reverse transcriptase to be inhibited thereby treating the organism.

The invention also relates to kits for use in synthesis, sequencing and amplification of nucleic acid molecules, comprising one or more containers containing one or more of the inhibitory nucleic acids or compositions of the invention. These kits of the invention may optionally comprise one or more additional components selected from the group consisting of one or more nucleotides, one or more polymerases (e.g., thermophilic or mesophilic DNA polymerases and/or reverse transcriptases), one or more suitable buffers, one or more primers and one or more terminating agents (such as one or more dideoxynucleotides). The invention also relates to kits for inhibiting viral replication or kits for treating viral infections comprising the inhibitory nucleic acids of the invention. Such kits may also comprise instructions or protocols for carrying out the methods of the invention.

Other preferred embodiments of the present invention will be apparent to one of ordinary skill in light of the following drawings and description of the invention, and of the claims.

DETAILED DESCRIPTION OF THE INVENTION

Definitions

Figure 1:
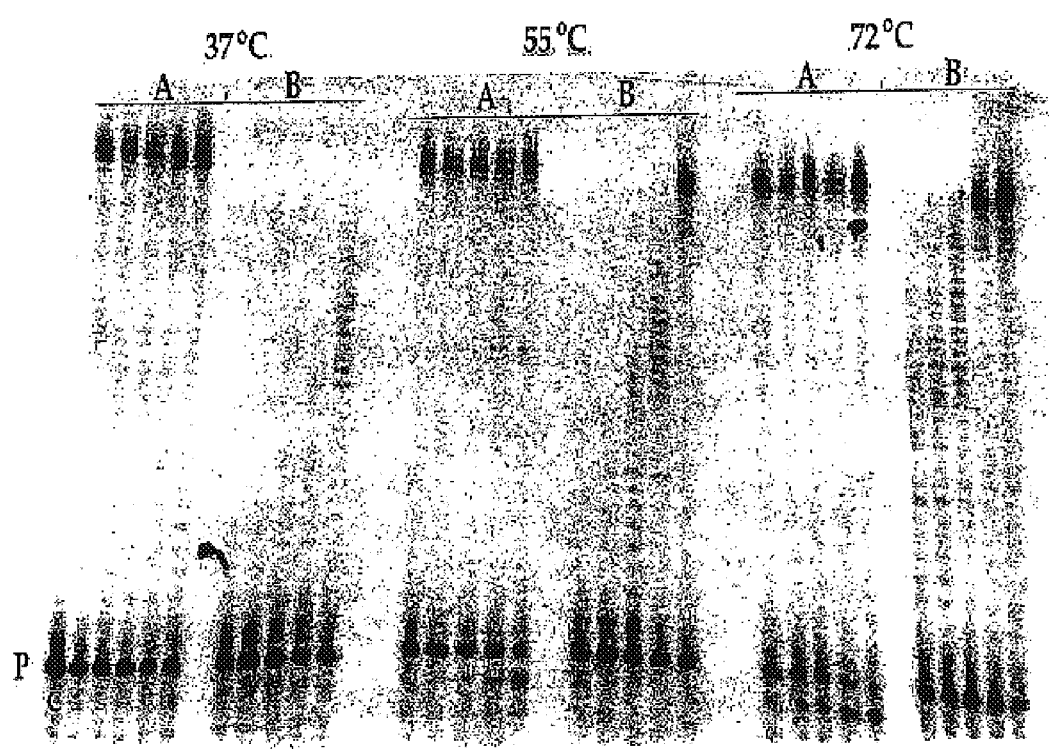
FIG. 1. The activity of Tne DNA polymerase was qualitatively determined. Panel A: determination in the absence of inhibitor A, Panel B: determination in the presence of inhibitor. The five lanes, of each panel, from left to right are 15 sec, 30 sec, 1 min, 2 min and 5 min time points that have elapsed before the reactions were quenched. P and C denote the primer position and control lane, respectively. Inhibitor A did not contain dideoxynucleotide at its termini.

In the description that follows, a number of terms used in recombinant DNA technology are utilized extensively. In order to provide a clearer and consistent understanding of the specification and claims, including the scope to be given such terms, the following definitions are provided.

Primer

As used herein, "primer" refers to a single-stranded oligonucleotide that is extended by covalent bonding of nucleotide monomers during amplification or polymerization of a DNA molecule.

Template

The term "template" as used herein refers to double-stranded or single-stranded nucleic acid molecules which are to be amplified, synthesized or sequenced. In the case of a double-stranded molecule, denaturation of its strands to form a first and second strand is preferably performed before these molecules may be amplified, synthesized or sequenced, or the double stranded molecule may be used directly as a template. For single stranded templates, a primer, complementary to a portion of the template is hybridized under appropriate conditions and one or more polymerases may then synthesize a nucleic acid molecule complementary to all or a portion of said template. Alternatively, for double stranded templates, one or more promoters (e.g. SP6, T7 or T3 promoters) may be used in combination with one or more polymerases to make nucleic acid molecules complementary to all or a portion of the template. The newly synthesized molecules, according to the invention, may be equal or shorter in length than the original template.

Incorporating

The term "incorporating" as used herein means becoming a part of a DNA and/or RNA molecule or primer.

Amplification

As used herein "amplification" refers to any in vitro method for increasing the number of copies of a nucleotide sequence with the use of a polymerase. Nucleic acid amplification results in the incorporation of nucleotides into a DNA and/or RNA molecule or primer thereby forming a new molecule complementary to a template. The formed nucleic acid molecule and its template can be used as templates to synthesize additional nucleic acid molecules. As used herein, one amplification reaction may consist of many rounds of replication. DNA amplification reactions include, for example, polymerase chain reactions (PCR). One PCR reaction may consist of 5 to 100 "cycles" of denaturation and synthesis of a DNA molecule.

Nucleotide

As used herein "nucleotide" refers to a base-sugar-phosphate combination. Nucleotides are monomeric units of a nucleic acid sequence (DNA and RNA). Nucleotides may also include mono-, di- and triphosphate forms of such nucleotides. The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Blocking Agent

"Blocking agent" refers to a nucleotide (or derivatives thereof), modified oligonucleotides and/or one or more other modifications which are incorporated into the nucleic acid inhibitors of the invention to prevent or inhibit degradation or digestion of such nucleic acid molecules by nuclease activity. One or multiple blocking agents may be incorporated in the nucleic acid inhibitors of the invention internally, at or near the 3' termini and/or at or near the 5' termini of the nucleic acid inhibitors. Preferably, such blocking agents are located, for linear inhibitor nucleic acid molecules, at or near the 3' termini and/or at or near the 5' termini and/or at the preferred cleavage position of the 5' to 3' exonuclease of such molecules (Lyamichev, V., Brow, M. A. D., and Dahlberg, J. E., (1993) Science, 260, 778–783). Preferably, such blocking agents prevent or inhibit degradation or digestion of the inhibitor nucleic acid molecules by exonuclease activity associated with the polymerase or reverse transcriptase used or that may be present in the synthesis reaction. For example, blocking agents for the invention prevent degradation or digestion of inhibitor nucleic acid molecules by 3' exonuclease activity and/or 5' exonuclease activity associated with a polymerase (e.g., a DNA polymerase). Preferred blocking agents in accordance with the invention include dideoxynucleotides and their derivatives such as ddATP, ddCTP, ddGTP, ddITP, and ddTTP. Other blocking agents for use in accordance with the invention include, but are not limited to, AZT, phosphamide backbones (e.g., PNAs), 3'-dNTPs (e.g., Condycepin) or any nucleotide containing a blocking group, preferably at its 3'-position. Such blocking agents preferably act to inhibit or prevent exonuclease activity (e.g., 3'-exonuclease activity) from altering or digesting the inhibitory nucleic acids of the invention. In some embodiments, the 5'-terminal of the oligonucleotides of the present invention may be modified in order to make them resistant to 5'-to-3' exonuclease activity. One such modification may be to add an addition nucleotide to the 5'-end of the oligonucleotide in a 5'-5'-linkage (see, Koza M. et al., *Journal of Organic Chemistry* 56:3757). This results in at the 5'-end of the oligonucleotide which results in the 5'-end having a 3. In another aspect, such blocking agents preferably inhibit or prevent polymerase activity of the polymerases from altering or changing (e.g., incorporating nucleotides) to the inhibitory nucleic acids of the invention.

Oligonucleotide

As used herein, "oligonucleotide" refers to a synthetic or biologically produced molecule comprising a covalently linked sequence of nucleotides which may be joined by a phosphodiester bond between the 3' position of the pentose of one nucleotide and the 5' position of the pentose of the adjacent nucleotide. Oligonucleotide as used herein is seen to include natural nucleic acid molecules (i.e., DNA and RNA) as well as non-natural or derivative molecules such as peptide nucleic acids, phophothioate containing nucleic acids, phosphonate containing nucleic acids and the like. In addition, oligonucleotides of the present invention may contain modified or non-naturally occurring sugar residues (i.e., arabainose) and/or modified base residues. Oligonucleotide is seen to encompass derivative molecules such as nucleic acid molecules comprising various natural nucleotides, derivative nucleotides, modified nucleotides or combinations thereof. Thus any oligonucleotide or other molecule useful in the methods of the invention are contemplated by this definition. Oligonucleotides of the present invention may also comprise blocking groups which prevent the interaction of the molecule with particular proteins, enzymes or substrates.

Hairpin

As used herein, the term "hairpin" is used to indicate the structure of an oligonucleotide in which one or more portions of the oligonucleotide form base pairs with one or more other portions of the oligonucleotide. When the two portions are base paired to form a double stranded portion of the oligonucleotide, the double stranded portion may be referred to as a stem. Thus, depending on the number of complementary portions used, a number of stems (preferably 1–10) may be formed. Additionally, formation of the one or more stems preferably allows formation of one or more loop structures in the hairpin molecule. In one aspect, any one or more of the loop structures may be cut or nicked at one or more sites within the loop or loops but preferably at least one loop is not so cut or nicked. The sequence of the oligonucleotide may be selected so as to vary the number of nucleotides which base pair to form the stem from about 3 nucleotides to about 100 or more nucleotides, from about 3 nucleotides to about 50 nucleotides, from about 3 nucleotides to about 25 nucleotides, and from about 3 to about 10 nucleotides. In addition, the sequence of the oligonucleotide may be varied so as to vary the number of nucleotides which do not form base pairs from 0 nucleotides to about 100 or more nucleotides, from 0 nucleotides to about 50 nucleotides, from 0 nucleotides to about 25 nucleotides or from 0 to about 10 nucleotides. The two portions of the oligonucleotide which base pair may be located anywhere or at any number of locations in the sequence of the oligonucleotide. In some embodiments, one base-pairing-portion of the oligonucleotide may include the 3'-terminal of the oligonucleotide. In some embodiments, one base-pairing-portion may include the 5'-terminal of the oligonucleotide. In some embodiments, one base-pairing-portion of the oligonucleotide may include the 3'-terminal while the other base-pairing-portion may include the 5'-terminal and, when base paired, the stem of the oligonucleotide is blunt ended. In other embodiments, the location of the base pairing portions of the oligonucleotide may be selected so as to form a 3'-overhang, a 5'-overhang and/or may be selected so that neither the 3'- nor the 5'-most nucleotides are involved in base pairing.

Hybridization

The terms "hybridization" and "hybridizing" refer to base pairing of two complementary single-stranded nucleic acid molecules (RNA and/or DNA and/or PNA) to give a double-stranded molecule. As used herein, two nucleic acid molecules may be hybridized although the base pairing is not completely complementary. Accordingly, mismatched bases do not prevent hybridization of two nucleic acid molecules provided that appropriate conditions, well known in the art, are used. In a preferred aspect, the double stranded inhibitory molecules are denatured under certain conditions such that the complementary single stranded molecules which are hybridized are allowed to separate. Single stranded molecules formed do not interact or bind polymerase or interact or bind polymerase with reduced efficiency compared to the corresponding double-stranded molecule.

Unit

The term "unit" as used herein refers to the activity of an enzyme. When referring, for example, to a DNA polymerase, one unit of activity is the amount of enzyme that will incorporate 10 nanomoles of dNTPs into acid-insoluble material (i.e., DNA or RNA) in 30 minutes under standard primed DNA synthesis conditions.

Viruses

As used herein, viruses that require a reverse transcriptase activity to complete their lifecycle are seen to include, but are not limited to, any member of the family retroviridae including human immunodeficiency viruses, bovine immunodeficiency virus, bovine leuukemia virus, human T-lymphotrophic viruses, caprine arthritis-encephalitis virus, equine infectious anemia virus, feline immunodeficiency virus, feline sarcoma and leukemia viruses, maedi/visna virus of sheep, mouse mammary tumor virus, simian immunodeficiency virus and other retroviruses known to those skilled in the art.

Vector

The term "vector" as used herein refers to a plasmid, phagemid, cosmid or phage nucleic acid or other nucleic acid molecule which is able to replicable autonomously in a host cell. Preferably a vector is characterized by one or a small number of restriction endonuclease recognition sites at which such nucleic acid sequences may be cut in a determinable fashion without loss of an essential biological function of the vector, and into which nucleic acid molecules may be spliced in order to bring about its replication and cloning. The cloning vector may further contain one or more markers suitable for use in the identification of cells transformed with the cloning vector. Markers, for example, are antibiotic resistance change genes, including, but not limited to tetracycline resistance or ampicillin resistance.

Expression Vector

The term "expression vector" as used herein refers to avector similar to a cloning vector but which is capable of enhancing the expression of a gene which has been cloned into it, after transformation into a host. The cloned gene is usually placed under the control of (i.e., operably linked to) certain control sequences such as promoter sequences.

Recombinant Host

The term "recombinant host" as used herein refers to any prokaryotic or eukaryotic microorganism which contains the desired cloned genes in an expression vector, cloning vector or any other nucleic acid molecule. The term "recombinant host" is also meant to include those host cells which have been genetically engineered to contain the desired gene on a host chromosome or in the host genome.

Host

The term "host" as used herein refers to any prokaryotic or eukaryotic microorganism that is the recipient of a replicable expression vector, cloning vector or any nucleic acid molecule including the inhibitory nucleic acid molecules of the invention. The nucleic acid molecule may contain, but is not limited to, a structural gene, a promoter and/or an origin of replication.

Promoter

The term "promote" as used herein refers to a DNA sequence generally described as the 5' region of a gene, located proximal to start the codon. At the promoter region, transcription of an adjacent gene(s) is initiated.

Gene

The term "gene" as used herein refers to a DNA sequence that contains information necessary for expression of a polypeptide or protein. It includes the promoter and the structural gene as well as other sequences involved in expression of the protein.

Structural Gene

The term "structural gene" as used herein refers to a DNA sequence that is transcribed into messenger RNA that is then translated into a sequence of amino acids characteristic of a specific polypeptide.

Operably Linked

The term "operably linked" as used herein means that the promoter is positioned to control the initiation of expression of the polypeptide encoded by the structural gene.

Expression

The term "expression" has used herein refers to the process by which a gene produces a polypeptide. It includes transcription of the gene into messenger RNA (mRNA) and the translation of such mRNA into polypeptide(s).

Substantially Pure

As used herein "substantially pure" means that the desired purified molecule such as a protein or nucleic acid molecule (including the inhibitory nucleic acid molecule of the invention) is essentially free from contaminants which are typically associated with the desired molecule. Contaminating components may include, but are not limited to, compounds or molecules which may interfere with the inhibitory or synthesis reactions of the invention, and/or that degrade or digest the inhibitory nucleic acid molecules of the invention (such as nucleases including exonucleases and endonucleases) or that degrade or digest the synthesized or amplified nucleic acid molecules produced by the methods of the invention.

Thermostable

As used herein "thermostable" refers to a DNA polymerase which is more resistant to inactivation by heat. DNA polymerases synthesize the formation of a DNA molecule complementary to a single-stranded DNA template by extending a primer in the 5'-3'-direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable DNA polymerase activity is more resistant to heat inactivation than a mesophilic DNA polymerase. However, a thermostable DNA polymerase docs not mean to refer to an enzyme which is totally resistant to heat inactivation and thus heat treatment may reduce the DNA polymerase activity to some extent. A thermostable DNA polymerase typically will also have a higher optimum temperature than mesophilic DNA polymerases.

3-to-5' Exonuclease Activity

"3'-to-5' exonuclease activity" is an enzymatic activity well known to the art. This activity is often associated with DNA polymerases and is thought to be involved in a DNA replication "editing" or correction mechanism.

A "DNA polymerase substantially reduced in 3'-to-5' exonuclease activity" is defined herein as either (1) a mutated DNA polymerase that has about or less than 10%, or preferably about or less than 1%, of the 3'-to-5' exonuclease activity of the corresponding unmutated, wild-type enzyme, or (2) a DNA polymerase having a 3'-to-5' exonuclease specific activity which is less than about 1 unit/mg protein, or preferably about or less than 0.1 units/mg protein. A unit of activity of 3'-to-5' exonuclease is defined as the amount of activity that solubilizes 10 nmoles of substrate ends in 60 min. at 37° C., assayed as described in the "BRL 1989 Catalogue & Reference Guide", page 5, with HhaI fragments of lambda DNA 3'-end labeled with [$^3$H]dTTP by terminal deoxynucleotidyl transferase (TdT). Protein is measured by the method of Brandford, Anal. Biochem. 72:248 (1976). As a means of comparison, natural, wild-type T5-DNA polymerase (DNAP) or T5-DNAP encoded by pTTQ19-T5-2 has a specific activity of about 10 units/mg protein while the DNA polymerase encoded by pTTQ19-T5-2(Exo-) (U.S. Pat. No. 5,270,179) has a specific activity of about 0.0001 units/mg protein, or 0.001% of the specific activity of the unmodified enzyme, a $10_5$-fold reduction. Polymerases used in accordance with the invention may lack or may be substantially reduced in 3' exonuclease activity.

5'-to-3' Exonuclease Activity

"5'-to-3' exonuclease activity" is also enzymatic activity well known in the art. This activity is often associated with DNA polymerases, such as E. coli PolI and Taq DNA polymerase.

A "polymerase substantially reduced in 5'-to-3' exonuclease activity" is defined herein as either (1) mutated or modified polymerase that has about or less than 10%, or preferably about or less than 1%, of the 5'-to-3' exonuclease activity of the corresponding unmutated, wild-type enzyme, or (2) a polymerase having 5'-to-3' exonuclease specific activity which is less than about 1 unit/mg protein, or preferably about or less than 0.1 units/mg protein.

Both of the 3'-to-5' and 5'-to-3' exonuclease activities can be observed on sequencing gels. Active 5'-to-3' exonuclease activity will produce different size products in a sequencing gel by removing mono-nucleotides and longer products from the 5'-end of the growing primers. 3'-to-5' exonuclease activity can be measured by following the degradation of radiolabeled primers in a sequencing gel. Thus, the relative amounts of these activities (e.g., by comparing wild-type and mutant or modified polymerases) can be determined with no more than routine experimentation.

Inhibitory Nucleic Acids

The nucleic acids of the present invention include single stranded and double stranded nucleic acids (although other strand multiples such as triple stranded (e.g., triple helix) molecules may be used) including nucleic acids comprised of DNA, RNA, PNA, LNA or other derivative nucleic acid molecules, or a combination thereof. The inhibitory nucleic acid comprises a sequence which is capable of forming a site at one set of conditions (preferably at ambient temperature) which competes with the template/primer substrate used in synthesis or amplification for binding an enzyme with polymerase activity and competes less efficiently under a second set of conditions (preferably elevated temperatures) for nucleic acid synthesis or amplification. Preferably, the sequence of the inhibitory nucleic acids is not complementary to the primer used in the synthesis, amplification or sequencing reaction to be inhibited. As will be recognized, other nucleic acids (natural, unnatural, modified etc.) may be selected and used in accordance with the invention. Such selection may be accomplished by binding studies and/or nucleic acid synthesis inhibition assays. Design of nucleic acid sequences for hairpin formation may be accomplished by those skilled in the art. See, e.g., Antao, V. P. and Tinoco, I., Jr., 1992, Nucl. Acids Res. 20: 819–824. Preferably, the nucleic acid inhibitor could be made nuclease resistant (3'-to-5' exonuclease and 5'-to-3' exonuclease) and/or inert to polymerization. Methods to render the nucleic acid inert to exonucleases and polymerization are known in the art and include, for example, using derivative nucleic acid molecules which may include derivative nucleotides (for example, using phosphamide and/or phosphorothioate backbone rather than phosphate) and/or addition of one or more blocking agents to the inhibitory nucleic acid molecules of the invention. The inhibitory nucleic acid preferably form one or more hairpin-loop structures with a double stranded stem. The double stranded stem can have blunt ends and/or a single stranded overhang (for example, at the 5' and/or 3' terminus) designed so as to mimic the typical primer/template substrate of a polymerase.

Inhibitory nucleic acids of the present invention are preferably used in the present compositions and methods at a final concentration in a synthesis, sequencing or amplification reaction sufficient to prevent or inhibit such synthesis, sequencing or amplification in the presence of a polymerase or reverse transcriptase enzyme. The ratio of inhibitory nucleic acids of the invention to polymerase or reverse transcriptase may vary depending on the polymerase or reverse transcriptase used. The molar ratio of inhibitory nucleic acids to polymerase/reverse transcriptase enzyme for a synthesis, sequencing or amplification reaction may range from about 0.001–100:1; 0.01–1000:1; 0.1–10,000:1; 1–100,000:1; 1–500,000:1; or 1–1,000,000:1. Of course, other suitable ratios of such inhibitory nucleic acids to polymerase/reverse transcriptase suitable for use in the invention will be apparent to one of ordinary skill in the art or determined with no more than routine experimentation.

Inhibitory nucleic acid molecules of the invention may be synthesized by standard chemical oligonucleotide synthesis techniques (for example, phosphoramidite and others know in the art, see U.S. Pat. No. 5,529,756). Alternatively, recombinant DNA techniques may be used to produce the inhibitory nucleic acids of the invention by cloning the nucleic acid molecule of interest into a vector, introducing the vector into the host cell, growing the host cell and isolating the inhibitory nucleic acid molecule of interest from the host cell. Inhibitory nucleic acid molecules of the invention may also be obtained from commercial sources of custom oligonucleotides such as Life Technologies, Inc. or may be made enzymaticly, for example, by using polymerases in nucleic acid synthesis or amplification reactions.

In some embodiments, the oligonucleotides of the present invention may be used for therapeutic purposes. In a preferred embodiment, the oligonucleotides of the present invention may be used to treat a subject (for example, a human or an animal) infected with a virus that requires reverse transcriptase activity to replicate. For therapeutic treatment, oligonucleotides may be administered as a pharmaceutically acceptable composition in which one or more oligonucleotides of the present invention may be mixed with one or more carriers, thickeners, diluents, buffers, preservatives, surface active agents, excipients and the like. Pharmaceutical compositions may also include one or more additional active ingredients such as antimicrobial agents, antiinflammatory agents, anesthetics, and the like in addition to oligonucleotides.

The pharmaceutical compositions of the present invention may be administered by any route commonly used to administer pharmaceutical compositions. For example, administration may be done topically (including opthalmically, vaginally, rectally, intranasally), orally, by inhalation, or parenterally, for example by intravenous drip or subcutaneous, intraperitoneal or intramuscular injection.

Pharmaceutical compositions formulated for topical administration may include ointments, lotions, creams, gels, drops, suppositories, sprays, liquids and powders. Any conventional pharmaceutical excipient, such as carriers, aqueous, powder or oily bases, thickeners and the like may be used.

Pharmaceutical compositions formulated for oral administration may be in the form of one or more powders, granules, suspensions or solutions in water or non-aqueous media, capsules, sachets, or tablets. Pharmaceutical compositions formulated for oral administration may additionally comprise thickeners, flavorings, diluents, emulsifiers, dispersing aids, binders or the like.

Pharmaceutical compositions formulated for parenteral administration may include sterile aqueous solutions which may also contain buffers, diluents and other suitable additives.

The pharmaceutical compositions of the present invention may be administered in a therapeutically effective dose. A therapeutically effective dose is one which inhibits the replication of the virus within the host. It is not necessary that replication of the virus be entirely eliminated in order for a treatment to be therapeutically effective. Reduction of the rate of replication of the virus may be a therapeutic effect. One or more doses of the pharmaceutical compositions of the present invention may be administered one or more times daily for a period of treatment which may be a single administration or may be multiple administrations per day for a period of several days to several months or until a cure is effected or a diminution of disease state is achieved. Persons of ordinary skill can easily determine optimum dosages, dosing routes and the frequency at which doses should be administered.

Polymerases. Enzymes with polymerase activity to which the inhibitory nucleic acids of the present invention can bind or interact include any enzyme used in nucleic acid synthesis, amplification or sequencing reactions. Such polymerases include, but are not limited to, polymerases (DNA and RNA polymerases), and reverse transcriptases. DNA polymerases include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polyernase, DEEPVENT™ DNA polymerase, *Pyrococcus woosii* (Pwo) DNA polymerase, Pyrococcus sp KOD2 (KOD) DNA polymerase, *Bacillus sterothermophilus* (Bst) DNA polymerase, *Bacillus caldophilus* (Bca) DNA polymerase, *Sulfolobus acidocaldarius* (Sac) DNA polyermase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), *E. coli* polI DNA polymerase, T5 DNA polymerase, T7 DNA polymerase, and generally polI type DNA polymerases and mutants, variants and derivatives thereof. RNA polymerases such as T3, T5 and SP6 and mutants, variants and derivatives thereof may also be used in accordance with the invention.

The nucleic acid polymerases used in the present invention may be mesophilic or thermophilic, and are preferably thermophilic. Preferred mesophilic DNA polymerases include polI family of DNA polymerases (and their respective Klenow fragments) any of which may be isolated from organism such as *E. coli, H. influenzae, D. radiodurans, H. pylori, C. aurantiacus, R. Prowazekii, T pallidum*, Synechocysis sp., *B. subtilis, L. lactis, S. pneumoniae, M. tuberculosis, M. leprae, M. smegmatis*, Bacteriophage L5, phi-C31, T7, T3, T5, SP01, SP02, mitochondrial from *S. cerevisiae* MIP-1, and eukaryotic *C. elegans*, and *D. melanogaster* (Astatke, M. et al., 1998, *J. Mol Biol.* 278, 147–165), polIII type DNA polymerase isolated from any sources, and mutants, derivatives or variants thereof, and the like. Preferred thermostable DNA polymerases that may be used in the methods and compositions of the invention include Taq, Tne, Tma, Pfu, KOD, Tfl, Tth Stoffel fragment, VENT™ and DEEPVENT™ DNA polymerases, and mutants, variants and derivatives thereof (U.S. Pat. Nos. 5,436,149; 4,889,818; 4,965,188; 5,079,352; 5,614,365; 5,374,553; 5,270,179; 5,047,342; 5,512,462; WO 92/06188; WO 92/06200; WO 96/10640; WO 97/09451; Barnes, W. M. Gene 112:29–35 (1992); Lawyer, F. C., et al, PCR Meth. Appl. 2:275–287 (1993); Flaman, J.-M, et al., Nucl. Acids Res. 22(15):3259–3260 (1994)).

Reverse transcriptases for use in this invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al, *Science* 239:487–491 (1988); U.S. Pat. Nos. 4,889,818 and 4,965,188), Tne DNA polymerase (WO 96/10640 and WO 97/09451), Tma DNA polymerase (U.S. Pat. No. 5,374,553) and mutants, variants or derivatives thereof (see, e.g., WO 97/09451 and WO 98/47912). Preferred enzymes for use in the invention include those that have reduced, substantially reduced or eliminated RNase H activity. By an enzyme "substantially reduced in RNase H activity" is meant that the enzyme has less than about 20%, more preferably less than about 15%, 10% or 5%, and most preferably less than about 2%, of the RNase H activity of the corresponding wildtype or RNase H+ enzyme such as wildtype Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al, *Nucl. Acids Res.* 16:265 (1988) and in Gerard, G. F., et al., *FOCUS* 14(5):91 (1992), the disclosures of all of which are fully incorporated herein by reference. Particularly preferred polypeptides for use in the invention include, but are not limited to, M-MLV H⁻ reverse transcriptase, RSV H⁻ reverse transcriptase, AMV H⁻ reverse transcriptase, RAV (rous-associated virus) H⁻ reverse transcriptase, MAV (myeloblastosis-associated virus) H⁻ reverse transcriptase and HIV H⁻ reverse transcriptase. (See U.S. Pat. No. 5,244,797 and WO 98/47912). It will be understood by one of ordinary skill, however, that any enzyme capable of producing a DNA molecule from a ribonucleic acid molecule (i.e., having reverse transcriptase activity) may be equivalently used in the compositions, methods and kits of the invention.

The enzymes having polymerase activity for use in the invention may be obtained commercially, for example from Life Technologies, Inc. (Rockville, Md.), Perkin-Elmer (Branchburg, N.J.), New England BioLabs (Beverly, Mass.) or Boehringer Mannheim Biochemicals (Indianapolis, Ind.). Enzymes having reverse transcriptase activity for use in the invention may be obtained commercially, for example, from Life Technologies, Inc. (Rockville, Md.), Pharmacia (Piscataway, N.J.), Sigma (Saint Louis, Mo.) or Boehringer Mannheim Biochemicals (Indianapolis, Ind.). Alternatively, polymerases or reverse transcriptases having polymerase activity may be isolated from their natural viral or bacterial sources according to standard procedures for isolating and purifying natural proteins that are well-known to one of ordinary skill in the art (see, e.g., Houts, G. E., et al., *j. Virol.* 29:517 (1979)). In addition, such polymerases/reverse transcriptases may be prepared by recombinant DNA techniques that are familiar to one of ordinary skill in the art (see, e.g., Kotewicz, M. L., et al., *Nucl. Acids Res.* 16:265 (1988); U.S. Pat. No. 5,244,797; WO 98/47912; Soltis, D. A., and Skalka, A. M., *Proc. Natl. Acad Sci. USA* 85:3372–3376 (1988)). Examples of enzymes having polymerase activity and reverse transcriptase activity may include any of those described in the present application.

Methods of Nucleic Acid Synthesis, Amplification and Sequencing

The inhibitory nucleic acids and compositions of the invention may be used in methods for the synthesis of nucleic acids. In particular, it has been discovered that the present inhibitory nucleic acids and compositions reduce nonspecific nucleic acid synthesis, particularly in amplification reactions such as the polymerase chain reaction (PCR). The present inhibitory nucleic acids and compositions may therefore be used in any method requiring the synthesis of nucleic acid molecules, such as DNA (including cDNA) and RNA molecules. Methods in which the inhibitory nucleic acids or compositions of the invention may advantageously be used include, but are not limited to, nucleic acid synthesis methods and nucleic acid amplification methods (including "hot-start" synthesis or amplification) where the reaction is set up at a temperature where the inhibitory nucleic acid can competitively inhibit DNA synthesis or amplification and the synthesis or amplification reaction is initiated by increasing the temperature to reduce the competitive inhibition by the inhibitor of the polymerases thus allowing nucleic acid synthesis or amplification to take place.

Nucleic acid synthesis methods according to this aspect of the invention may comprise one or more steps. For example, the invention provides a method for synthesizing a nucleic acid molecule comprising (a) mixing a nucleic acid template with one or more primers and one or more inhibitory nucleic acids of the present invention (which may be the same or different) and one or more enzymes having polymerase or reverse transcriptase activity to form a mixture; (b) incubating the mixture under conditions sufficient to inhibit or prevent nucleic acid synthesis; and (c) incubating the mixture under conditions sufficient to make a first nucleic acid molecule complementary to all or a portion of the template. According to this aspect of the invention, the nucleic acid template may be a DNA molecule such as a cDNA molecule or library, or an RNA molecule such as a mRNA molecule or population of molecules. Conditions sufficient to allow synthesis such as pH, temperature, ironic strength, and incubation times may be optimized according to routine methods known to those skilled in the art.

In accordance with the invention, the input or template nucleic acid molecules or libraries may be prepared from populations of nucleic acid molecules obtained from natural sources, such as a variety of cells, tissues, organs or organisms. Cells that may be used as sources of nucleic acid molecules may be prokaryotic (bacterial cells, including those of species of the genera Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, and Streptomyces) or eukaryotic (including fungi (especially yeasts), plants, protozoans and other parasites, and animals including insects (particularly Drosophilia spp. cells), nematodes (particularly *Caenorhabditis elegans* cells), and mammals (particulary human cells)).

Once the starting cells, tissues, organs or other samples are obtained, nucleic acid molecules (such as DNA, RNA (e.g., mRNA or polyA+RNA) molecules) may be isolated, or cDNA molecules or libraries prepared therefrom, by methods that are well-known in the art (See, e.g. Maniatis, T., et al., Cell 15:687–701 (1978); Okayama, H., and Berg, P., Mol. Cell. Biol. 2:161–170 (1982); Gubler, U., and Hoffman, B. J., Gene 25:263–269 (1983)).

In the practice of a preferred aspect of the invention, a first nucleic acid molecule may be synthesized by mixing an nucleic acid template obtained as described above, which is preferably a DNA molecule or an RNA molecule such as an mRNA molecule or a polyA+RNA molecule, with one or more of the above-described enzymes with polymerase activity to which has been added the inhibitory nucleic acids or compositions of the invention to form a mixture. Synthesis of a first nucleic acid molecule complementary to all or a portion of the nucleic acid template is preferably accomplished after raising the temperature of the reaction and thus reducing the competitive inhibition of the inhibitory nucleic acid of the present invention thereby favoring the reverse transcription (in the case of an RNA template) and/or polymerization of the input or template nucleic acid molecule. Such synthesis is preferably accomplished in the presence of nucleotides (e.g., deoxyribonucleoside triphosphates (dNTPs), dideoxyribonucleoside triphosphate (ddNTPs) or derivatives thereof).

Of course, other techniques of nucleic acid synthesis in which the inhibitory nucleic acids, compositions and methods of the invention may be advantageously used will be readily apparent to one of ordinary skill in the art.

In other aspects of the invention, the inhibitory nucleic acids and compositions of the invention may be used in methods for amplifying or sequencing nucleic acid molecules. Nucleic acid amplification methods according to this aspect of the invention may additionally comprise use of one or more polypeptides having reverse transcriptase activity, in methods generally known in the art as one-step (e.g., one-step RT-PCR) or two-step (e.g., two-step RT-PCR) reverse transcriptase-amplification reactions. For amplification of long nucleic acid molecules (e.g., greater than about 3–5 Kb in length), a combination of DNA polymerases may be used, as described in WO 98/06736 and WO 95/16028.

Amplification methods according to this aspect of the invention may comprise one or more steps. For example, the invention provides a method for amplifying a nucleic acid molecule comprising (a) mixing one or more enzymes with polymerase activity with the inhibitory nucleic acids or compositions of the invention and one or more nucleic acid templates; (b) incubating the mixture under conditions sufficient to inhibit or prevent nucleic acid amplification; and (c) incubating the mixture under conditions sufficient to allow the enzyme with polymerase activity to amplify one or more nucleic acid molecules complementary to all or a portion of the templates. The invention also provides nucleic acid molecules amplified by such methods.

General methods for the amplification and analysis of nucleic acid molecules or fragments are well-known to one of ordinary skill in the art (see e.g., U.S. Pat. Nos. 4,683,195; 4,683,202; and 4,800,159; Innis, M. A., et al., eds., PCR Protocols: A Guide to Methods and Applications, San Diego, Calif.: Academic Press, Inc. (1990); Griffin, H. G., and Griffin, A. M., eds., PCR Technology: Current Innovations, Boca Raton, Fla.: CRC Press (1994)). For example, amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), Nucleic Acid Sequenced-Based Amplification (NASBA; U.S. Pat. No. 5,409,818; EP 0 329 822).

Typically, these amplification methods comprise: (a) mixing one or more enzymes with polymerase activity with one or more inhibitory nucleic acids of the present invention to form a complex (protein-nucleic acid); (b) mixing the nucleic acid sample with the complex of (a) in the presence of one or more primer sequences; and (c) amplifying the nucleic acid sample to generate a collection of amplified nucleic acid fragments, preferably by PCR or equivalent automated amplification technique.

Following amplification or synthesis by the methods of the present invention, the amplified or synthesized nucleic acid fragments may be isolated for further use or characterization. This step is usually accomplished by separation of the amplified or synthesized nucleic acid fragments by size or by any physical or biochemical means including gel electrophoresis, capillary electrophoresis, chromatography (including sizing, affinity and immunochromatography), density gradient centrifugation and immunoadsorption. Separation of nucleic acid fragments by gel electrophoresis is particularly preferred, as it provides a rapid and highly reproducible means of sensitive separation of a multitude of nucleic acid fragments, and permits direct, simultaneous comparison of the fragments in several samples of nucleic acids. One can extend this approach, in another preferred embodiment, to isolate and characterize these fragments or any nucleic acid fragment amplified or synthesized by the methods of the invention. Thus, the invention is also directed to isolated nucleic acid molecules produced by the amplification or synthesis methods of the invention.

In this embodiment, one or more of the amplified or synthesized nucleic acid fragments are removed from the gel which was used for identification (see above), according to standard techniques such as electroelution or physical excision. The isolated unique nucleic acid fragments may then be inserted into standard vectors, including expression vectors, suitable for transfection or transformation of a variety of prokaryotic (bacterial) or eukaryotic (yeast, plant or animal including human and other mammalian) cells. Alternatively, nucleic acid molecules produced by the methods of the invention may be further characterized, for example by sequencing (e.g., determining the nucleotide sequence of the nucleic acid fragments), by methods described below and others that are standard in the art (see, e.g., U.S. Pat. Nos. 4,962,022 and 5,498,523, which are directed to methods of DNA sequencing).

Nucleic acid sequencing methods according to the invention may comprise one or more steps. For example, the invention provides a method for sequencing a nucleic acid molecule comprising (a) mixing an enzyme with polymerase activity with one or more inhibitory nucleic acids of the present invention, a nucleic acid molecule to be sequenced, one or more primers, one or more nucleotides, and one or more terminating agents (such as a dideoxynucleotide) to form a mixture; (b) incubating the mixture under conditions sufficient to inhibit or prevent nucleic acid sequencing or synthesis; (c) incubating the mixture under conditions sufficient to synthesize a population of molecules complementary to all or a portion of the molecule to be sequenced; and (d) separating the population to determine the nucleotide sequence of all or a portion of the molecule to be sequenced.

Nucleic acid sequencing techniques which may employ the present inhibitory molecules or compositions include dideoxy sequencing methods such as those disclosed in U.S. Pat. Nos. 4,962,022 and 5,498,523.

Vectors and Host Cells

The present invention also relates to vectors which comprise an inhibitory nucleic acid molecule of the present invention. Further, the invention relates to host cells which contain the inhibitory nucleic acids of the invention and preferably to host cells comprising recombinant vectors containing such nucleic acids, and to methods for the production of the nucleic acids of the invention using these vectors and host cells. Nucleic acid synthesis and amplification products produced by the methods of the invention may also be cloned into vectors and host cells in accordance with the invention to facilitate production of such nucleic acid molecules or proteins encoded by such nucleic acid molecules.

The vectors will preferably include at least one selectable marker. Such markers include, but are not limited to, antibiotic resistance genes such as tetracycline or ampicillin resistance genes for culturing in *E. coli* and other bacteria. Representative examples of appropriate host cells include, but are not limited to, bacterial cells such as *E. coli*, Streptomyces spp., Erwinia spp., Klebsiella spp and *Salmonella typhimurium*. Preferred as a host cell is *E. coli*, and particularly preferred are *E. coli* strains DH10B and Stbl2, which are available commercially (Life Technologies, Inc., Rockville, Md.).

Nucleic Acid Production

As noted above, the methods of the present invention are suitable for production of any nucleic acid or any protein encoded by such nucleic acid molecule, via insertion of the above-described nucleic acid molecules or vectors into a host cell and isolation of the nucleic acid molecule from the host cell or isolation of the protein from the host cell expressing the nucleic acid molecule. Introduction of the nucleic acid molecules or vectors into a hot cell to produce a transformed host cell can be effected by calcium phosphate transfection, calcium chloride transformation, DEAE-dextran mediated transfection, cationic lipid-mediated transfection, electroporation, transduction, infection or other methods. Such methods are described in many standard laboratory manuals, such as Davis, et al, Basic Methods in Molecular Biology (1986). Preferably, chemically competent or electrocompetent cells are used for such transformation reactions. Once transformed host cells have been obtained, the cells may be cultivated under any physiologically compatible conditions of pH and temperature, in any suitable nutrient medium containing assimilable sources of carbon, nitrogen and essential minerals that support host cell growth. For example, certain expression vectors comprise regulatory regions which require cell growth at certain temperatures, or addition of certain chemicals or inducing agents to the cell growth. Appropriate culture media and conditions for the above-described host cells and vectors are well-known in the art. Following its production in the host cells, the nucleic acid or protein of interest may be isolated by several techniques. To liberate the nucleic acid or protein of interest from the host cells, the cells are preferably lysed or ruptured. This lysis may be accomplished by contacting the cells with a hypotonic solution, by treatment with a cell wall-disrupting enzyme such as lysozyme, by sonication, by treatment with high pressure, or by a combination of the above methods. Other methods of bacterial cell disruption and lysis that are known to one of ordinary skill may also be used.

Following disruption, the nucleic acid or proteins may be separated from the cellular debris by any technique suitable for separation of particles in complex mixtures. The nucleic acids or proteins may then be purified by well known isolation techniques. Suitable techniques for purification include, but are not limited to, ammonium sulfate or ethanol precipitation, acid extraction, electrophoresis, immunoadsorption, CsCl centrifugation, anion or cation exchange chromatography, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hybroxylapatite chromatography and lectin chromatography.

Kits

The present invention also provides kits for use in the synthesis, amplification or sequencing of nucleic acid molecules. Kits according to this aspect of the invention may comprise one or more containers, such as vials, tubes, ampules, bottles and the like, which may comprise one or more of the inhibitory nucleic acids and/or compositions of the invention.

The kits of the invention may comprise one or more of the following components: (i) one or more nucleic acids or compositions of the invention; (ii) one or more polymerases and/or reverse transcriptases, (iii) one or more suitable buffers or buffering salts; (iv) one or more nucleotides; and (v) one or more primers.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Nucleic Acid Inhibitors

Nucleic acid inhibitors were synthesized by Life Technologies, Inc. and were HPLC or PAGE purified.
Nucleic Acid Inhibitor A (34-mer)
5'CCCAATATGGACCGGTCGAAAGACCGGTCCATAT3' (SEQ ID NO:1)
Nucleic Acid Inhibitor B (55-mer)
5'CCATGCAGGTAGCCGATGAACTGGTC-GAAAGACCAGTTCATCGGCTACCTGCATG3' (SEQ ID NO:2)

At ambient temperature the above sequences form a hairpin-like structure (Antao an dTinoco, 1992, supra), see structures below.

In some embodiments, the 3'-terminus of Inhibitor A may be capped at the 3' terminus with a dideoxythymine triphosphate using a Klenow fragment mutatn (F762Y) of DNA polymerase I (*Escherichia coli*) or T7 DNA polymerase (Tabor, S. and Richardson, C. C., 1995, *Proc. Natl. Acad Sci. USA* 92, 6339–6343). The 3'-OH terminus of the oligonucleotide was extended with ddTTP by the polymerase at 20 $\mu$M ddTTP in the presence of 2 mM $Mg^{2+}$ in 50 mM Tris pH 7.5 buffer, at 37° C. for 30 min. Following extension, the sample was placed in a 100° C. water bath for 3 min to denature the protein. Following heating the oligonucleotide sample was cooled slowly to ambient temperature (2–3 hrs) to allow formation of the hairpin structure.

Nucleic Acid Inhibitor A as Hairpin Structure:

```
    A                            (SEQ ID NO:1)
  A GACCGGTCCATAT
  A CTGGCCAGGTATAACCC⁵'
    G
```

Nucleic Acid Inhibitor B as Hairpin Structure

```
    A                            (SEQ ID NO:2)
  A GACCAGTTCATCGGCTACCTGCATG
  A CTGGTCAAGTAGCCGATGGACGTACC⁵'
    G
```

In some embodiments, the nucleic acid inhibitor B may be capped at the 3' terminus by ddGTP as described above.

This invention was tested using Tne DNA polymerase—a thermostable DNA polymerase that is significantly efficient at low temperature in incorporating deoxynucleotides into the growing strand, about 50-fold more efficient than Taq DNA polymerase at 37° C. The Tne used was wild type except that it was rendered substantially reduced in 5' to 3' exonuclease activity by virtue of D137A mutation (See WO 98/09451).

EXAMPLE 2

Inhibition of Polymerase with Inhibitor

The time course of the activity of Tne DNA polymerase was qualitatively determined using a 34/60-mer primer/template substrate at 3 different temperatures. FIG. 1 represents results from these experiments. For each temperature, polymerase activity was measured in the absence (Panel A) and presence (Panel B) of inhibitor A.

Aliquots of the reaction mixture were taken at various time points and separated on an agarose gel. The five lanes, of each panel, from left to right at 15 sec, 30 sec, 1 min, 2 min and 5 min, time points that have elapsed before the reactions were quenched. P and C denote the primer position and control lane, respectively.

As can be seen in FIG. 1, the potency of the inhibition of the polymerase reaction catalyzed by Tne is significantly reduced as the temperature is increased.

EXAMPLE 3

Amplification of a Target DNA Sequence from Plasmid DNA Source

Figure 2:
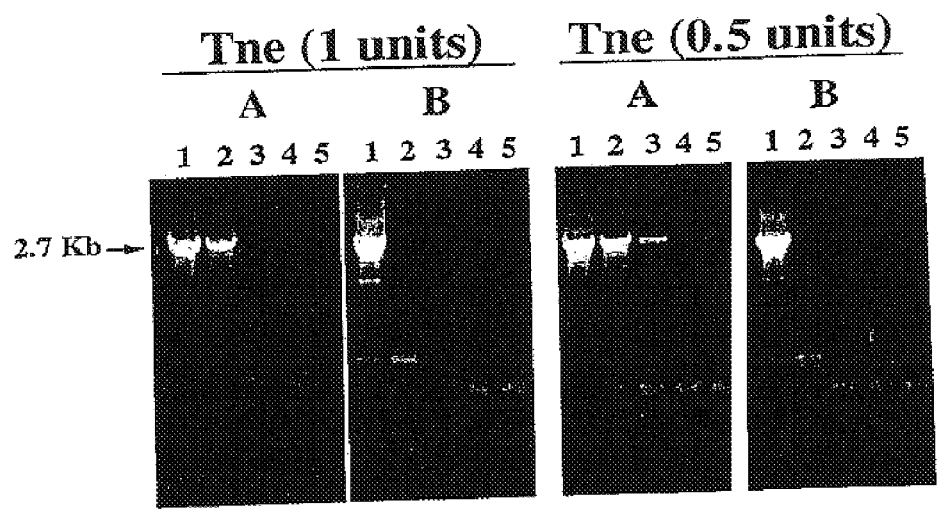
FIG. 2. Amplification of a 2.7 Kb target DNA sequence (pUC19) was performed at 5 different dilutions of the template. The target was amplified by Tne DNA polymerase. Two different concentration of Tne polymerse (85 nM and (e.g, 1 unit) and 42.5 nM (e.g., 0.5 units)) and the respective inhibitor B Complexes (using a 150-fold excess hairpin B over the polymerase concentration) were used for each amplification condition. The concentration of the target DNA in lanes 1, 2, 3, 4 & 5 is 100 pg, 20 pg, 2 pg, 0.2 pg and 0.02 pg, respectively. Inhibitor B did not contain dideoxynucleotide at its termini.

A 2.7 Kb target DNA sequence delivered from pUC19 plasmid was amplified using 5 different dilutions of the template. The target was amplified by Tne DNA polymerases. Two different concentration of Tne polymerase (85 nM (e.g., 1 unit) and 42.5 nM (i.e., 0.5 units) and the Tne complexed to the inhibitor nucleic acid (using a 150-fold excess inhibitor B over polymerase) were used at each amplification condition. The results are shown in FIG. 2. The concentration of the target DNA in lanes 1, 2, 3, 4 and 5 denote 100 pg, 20 pg 2 pg, 0.2 pg and 0.02 pg, respectively.

Results indicate that the sensitivity of Tne was greatly improved by the addition of the inhibitor, and relative purity of the target molecule was immensely enhanced.

EXAMPLE 4

Amplification of a Target DNA Sequence from Genomic DNA Source

Figure 3:
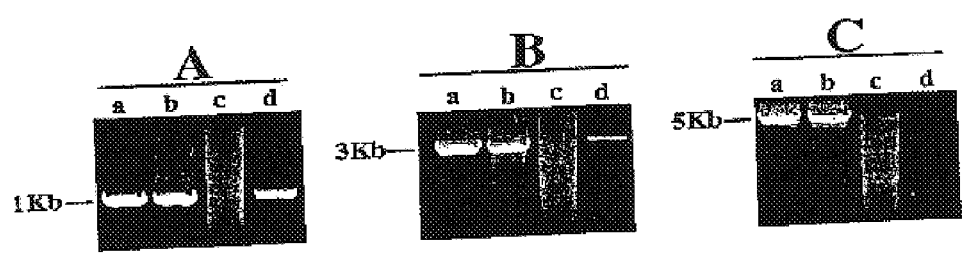
FIG. 3. A 1 Kb, 3 Kb and 5 Kb target DNA sequence (human genomic source) were amplified by Tne (85 nM (e.g., 1 unit) and Taq (e.g., 1 unit)) DNA polymerases as represented in panels A, B, and C respectively. The four lanes of each panel repersented as a, b, c and d are Tne (+125-fold excess inhibitor A), Tne (+50-fold excess inhibitor A), Tne (no inhibitor) and Taq (no inhibitor), respectively. Inhibitor A contained a 3'-terminal dideoxynucleotide (i.e., ddT).

A 1 Kb, 3 Kb and 5 Kb target DNA sequences were amplified by Tne (85 nM (e.g., 1 unit) and Taq (1 unit) DNA polymerases as represented in panels A, B and C of FIG. 3, respectively. The four lanes of each panel represented as a, b, c and d are Tne (+125-fold excess inhibitor A (ddT capped)), Tne (+50-fold excess inhibitor A (ddT capped)), Tne (no inhibitor) and Taq (no inhibitor), respectively.

Results indicate that the sensitivity of Tne was greatly improved by the addition of the inhibitor and relative purity of the target molecule was immensely improved for each target condition.

EXAMPLE 5

Amplification of a 5 and 15 Kb Target DNA Sequence by Tne DNA Polymerase

Figure 4:
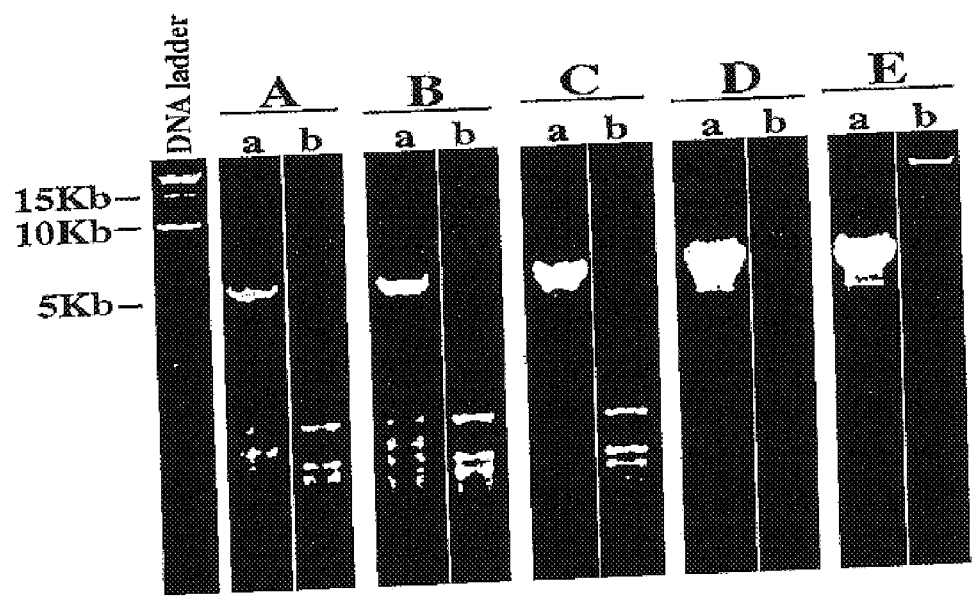
FIG. 4. The amplification of a 5 and 15 Kb target DNA sequence (human genomic source) was performed with Tne DNA polymerase (8.5 nM (e.g., 0.1 units)). The five panels A, B, C, D and E represent reaction conditions: Tne (no inhibitor), Tne (+50-fold excess inhibitor), Tne (+150-fold excess inhibitor), Tne (+300-fold excess inhibitor), Tne (+750-fold excess inhibitor), respectively. The two lanes (a and b) for each panel represent amplification of a target size of 5 and 15 Kb. For this assay, the inhibitor B was used which did not contain a terminal dideoxynucleotide.

The five panels A, B, C, D and E of FIG. 4 represent reaction conditions: control Tne (no inhibitor), Tne (+50-fold excess inhibitor B), Tne (+150-fold excess inhibitor B), Tne (+300-fold excess inhibitor B), Tne (+750-fold excess inhibitor B), respectively. The two lanes in each panel represented as A and B are for amplification of target size of 5 and 15 Kb. The final concentration of the Tne DNA polymerase in each reaction was 8.5 nM (e.g., 0.1 unit).

As can be seen in FIG. 4, the sensitivity of Tne was greatly improved by the addition of this inhibitor, and relative purity of the target molecule was immensely improved as the concentration of the inhibitor was optimized. As shown in panels D and E, 15 Kb product can only be amplified by Tne DNA polymerase, under Taq PCR conditions (Perkin-Elmer), in the presence of the inhibitor nucleic acid.

EXAMPLE 6

Figure 5:
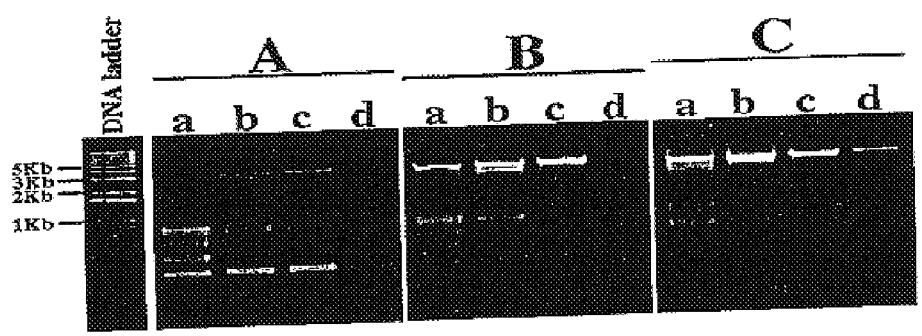
FIG. 5. The amplification of a 3 Kb target DNA sequence (human genomic source) was performed with 1 unit Taq DNA polymerase. The three panels A, B, and C represent reaction conditions: for A and B the same primer sequences were used—I) the PCR mix was incubated at 94° C. for 1 min and was set on ice to force mis-priming. All PCR reactions were set for 30 min at 25° C. so as to increase non-specific DNA synthesis. Each condition has four lanes-lane a (Taq control), b (Taq+16 nM inhibitor), c (Taq+32 nM inhibitor) and d (Taq+64 nM inhibitor). Inhibitor B was used which did not contain a terminal dideoxynucleotide.

Amplification of a 3 Kb Target DNA Sequence (Human Genomic Source) by 1 Unit Taq DNA Polymerase The three panels A, B, and C of FIG. 5 represent reaction conditions. For A and B, the same primer sequences were used. In A, the PCR mix was incubated at 94° C. for 1 min and was set on ice to force mis-priming. All PCR reaction were set for 30 min at 25° C. so as to increase non-specific DNA synthesis. Each condition: lane A (Taq control), B (Taq+126 nM inhibitor), C (Taq+32 nM inhibitor) and D (Taq+64 nM inhibitor).

Results show that the specificity of Taq was greatly improved by the addition of the inhibitor in each case producing significant reduction in the non-specific DNA synthesis and enhanced amount of the target sequence product.

EXAMPLE 7

Inhibition of RT Using the Oligonucleotides of the Present Invention

The DNA polymerase activity of ThermoScript™ I RNase deficient mutant reverse transcriptase (RT) (available from Life Technologies, Inc.) was determined at ambient temperature, 37° C. and 55° C. in the presence and absence of the oligonucleotide inhibitor molecules. The sequences and secondary structures of the oligonucleotide inhibitors are shown below. The polymerase activity of the RT was determined under steady state kinetic conditions using olig $(dG)_{15}$/polyrC as the primer/template substrate. This assay has been described by Polesky et al. (1990), and was used with minor modification.

Oligonucleotide Inhibitors

All nucleic acid inhibitors used in our assays were HPLC purified, and were capped synthetically with phosphate $(PO_{4-})$ at the 3' terminus. The mis-matches on the double stranded portion of the molecules were introduced in order to reduce the melting temperature of the double stranded without affecting the length of the nucleic acid inhibitors. Nucleic acid inhibitor H is a control oligonucleic acid that does not form double stranded structure under our experimental condition and is used to determine the level of inhibition by the RNA sequence.

Nucleic Acid Inhibitor C (Synthesized by Synthetic Genetics)

A 17/27 mer DNA/DNA double stranded nucleic acid inhibitor.

5'GGTATAGTAATAATATA3'
3'CCATATCATTATTATATATGTAATTAA5' (SEQ ID NO:3)

Nucleic Acid Inhibitor D (Synthesized by Life Technologies, Inc.)

A 50 mer Dna/RNA hybrid nucleic acid, RNA bases are underlined.

5'AAUUAAUGUAUAUAUUAUUACUAUACCGAAGG
GTATAGTAATAATATATA5' (SEQ ID NO:4)

Hairpin Structure of Nucleic Acid Inhibitor D

```
       G                                    (SEQ ID NO:4)
     A GGTATAGTAATAATATATA-3'
     A CCAUAUCAUUAUUAUAUAUGUAAUUAA-5'
       G
```

Nucleic Acid Inhibitor E (Synthesized by Life Technologies, Inc.)

A 50 mer DNA/RNA hybrid nucleic acid, RNA bases are single underline and the two mis-match positions are double underlined on the DNA portion of the corresponding hairpin structure.

5'<u>AAUUAAUGUAUAUAUUAUUACUAUA</u>CCGAAGG GTATAATAATAGTATATA3' (SEQ ID NO:5)

Hairpin Structure of Nucleic Acid Inhibitor E

```
       G                                      (SEQ ID NO:5)
    A GGTATA<u>A</u>TAATA<u>G</u>TATATA-3'
    A CC<u>AUAUCAUUAUUAUAUAUGUAAUUAA</u>-5'
       G
```

Nucleic Acid Inhibitor F (Synthesized by Life Technologies, Inc.)

A 50 mer DNA/RNA hybrid nucleic acid, RNA bases are single underlined and the three mis-match positions are double underlined on the DNA portion of the corresponding hairpin structure.

5'<u>AAUUAAUGUAUAUAUUAUUACUAUA</u>CCGAAGG GTATAATGAGAGTATATA3' (SEQ ID NO:6)

Hairpin Structure of Nucleic Acid Inhibitor F

```
       G                                      (SEQ ID NO:6)
    A GGTATA<u>A</u>T<u>GA</u>GA<u>G</u>TATATA-3'
    A CC<u>AUAUCAUUAUUAUAUAUGUAAUUAA</u>-5'
       G
```

Nucleic Acid Inhibitor G (Synthesized by Life Technologies, Inc.

A 50 mer DNA/RNA hybrid nucleic acid, RNA bases are underlined and the four mis-match positions are double underlined on the DNA portion of the corresponding hairpin structure.

5'<u>AAUUAAUGUAUAUAUUAUUACUAUA</u>CCGAAGG GTATAATGAGAGTATATA3' (SEQ ID NO:7)

Hairpin Structure of Nucleic Acid Inhibitor G

```
       G                                      (SEQ ID NO:7)
    A GGTATA<u>A</u>T<u>GA</u>GA<u>G</u>TATATA-3'
    A CC<u>AUAUCAUUAUUAUAUAUGUAAUUAA</u>-5'
       G
```

Nucleic Acid Inhibitor H (Synthesized by Life Technologies, Inc.)

A 50 mer DNA/RNA hybrid nucleic acid, RNA bases are underlined.

5'<u>AAUUAAUGUAUAUAUUAUUACUAUA</u>CCGAAAAT ATATAATGATGATATAG3' (SEQ ID NO:8)

The relative polymerase activities of ThermoScript™ I in the absence and presence of nucleic acid inhibitors at ambient temperature (~22° C.), 37° C. and 55° C was determined. The polymerization reaction was initiated by the addition of RT or RT/inhibitor (5 μL) to a solution of the primer/template in the presence of dGTP (spiked with dGT$^{32}$P) and MgCl$_2$, final reaction volume of 50 μL. The mixture was incubated at the reaction temperature, and samples (5 μL) were removed at 1 min (22° C.) and 15 sec (37° C. and 55° C.) intervals and were added into 50 μL of 25 mM EDTA. A portion of the quenched solution was applied to DE-81 filters. Following washes to remove unincorporated dGTP, the filters were counted in scintillation vials containing EconoFluor-2 (Packard). The apparent rate of the reaction was derived from the rate plot (corn plotted against time interval). The reaction concentration of the oligo(dG)$_{15}$/polyrC was 800 nM in primer, dGTP was 100 μM and MgCl$_2$ and KCl were 10 mM and 50 mM, respectively. For each reaction condition the concentration of the reverse transcriptase was maintained at 12 nM whereas the concentration of each of the oligonucleotide inhibitor was 540 nM.

Figure 6A:
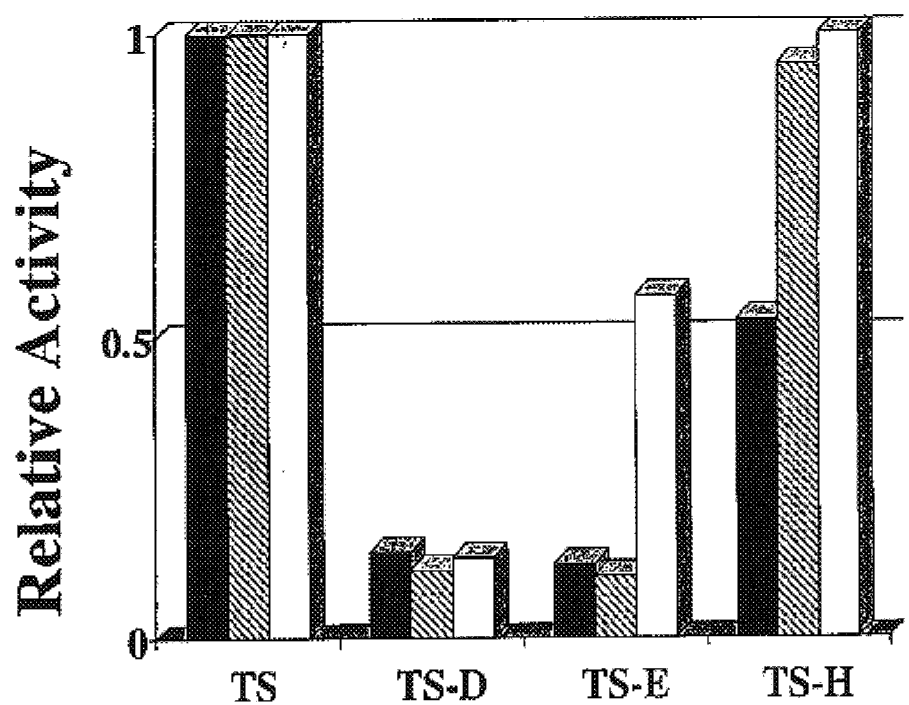
FIG. 6A is a graph showing the results of polymerase activity assays of Thermoscript™ I in the absence and presence of nucleic acid inhibitors at ambient temperature (left bar), 37° C. (center bar) and 55° C. (right bar). TS denotes polymerase reaction initiated by Thermoscript™ I, TS-D denotes polymerase reaction initiated by Thermoscript™ I in the presence of nucleic acid inhibitor D, TS-E denotes polymerase reaction initiated by Thermoscript™ in the presence of nucleic acid inhibitor E, and TS-H denotes polymerase reaction initiated by Thermoscript™ I in the presence of nucleic acid inhibitor H.
Figure 6B:
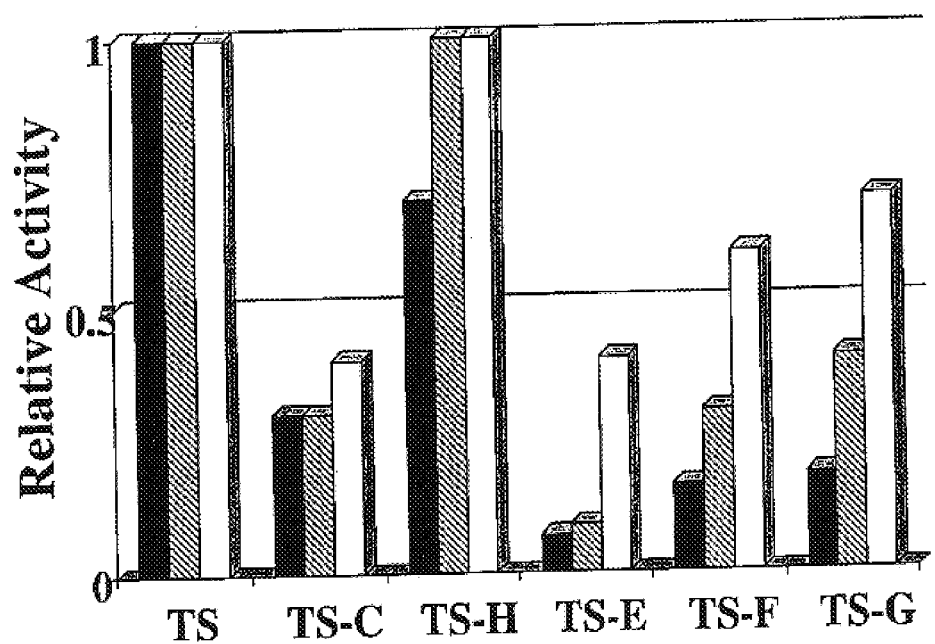
FIG. 6B is a graph showing the results of polymerase activity assays of Thermoscript™ I in the absence and presence of nucleic acid inhibitors at ambient temperature (left bar), 37° C. (center bar) and 55° C. (right bar). TS denotes polymerase reaction initiated by Thermoscript™ I, TS-D denotes polymerase reaction initiated by Thermoscript™ I in the presence of nucleic acid inhibitor C, TS-H denotes polymerase reaction initiated by Thermoscript™ I in the presence of nucleic acid inhibitor H, TS-E denotes polymerase reaction initiated by Thermoscript™ I in the presence of nucleic acid inhibitor E, TS-F denotes polymerase reaction initiated by Thermoscript™ I in the presence of nucleic acid inhibitor F, and TS-G denotes polymerase reaction initiated by Thermoscript™ I in the presence of nucleic acid inhibitor G.

The relative activity of the polymerization reaction catalyzed by ThermoScript™ at ambient temperature, 37° C. and 55° C. in the presence and absence of the inhibitors are shown in FIGS. 6A and 6B. The activities in the absence of the oligonucleotide inhibitors (free ThermoScript™ I) was normalized to 1 for measurements at each temperature. The RT activity in the presence of an inhibitor was correlated to the activity of ThermoScript™ at each temperature and the relative normalized activities are presented as a bar graph and are shown in FIGS. 6A and 6B. For each set of reaction condition, the three bars from left to right denote reactions performed at ambient temperature, 37° C. and 55° C., respectively. TS, TS-D, TS-E, and TS-H in FIG. 6A denote polymerase reaction initiated by ThermoScript™ I, ThermoScript™ I-nucleic acid inhibitor D complex, ThermoScript™ I-nucleic acid inhibitor E complex and ThermoScript™ I-nucleic acid inhibitor H complex, respectively. The efficiency of inhibition of the RT activity is dependent to the temperature which indicates that the level of inhibition of RT by the nucleic acid inhibitors is dependent to the melting temperature of the nucleic acid.

Nucleic Acid Inhibitor D

Under experimental conditions described above, complexing ThermoScript™ I with about 50-fold excess of this nucleic acid prior to initiating the polymerization reaction inhibited the RT activity by about 85–90% at each of the reaction temperatures. The relative similarity of the level of inhibition is indicative of the stability of the hairpin structure of this nucleic acid inhibitor in the temperature range that was assayed for RT activity.

Nucleic Acid Inhibitor E

Under the experimental conditions, complexing ThermoScript™ I with about 50-fold excess of this nucleic acid prior to initiating the polymerization reaction inhibited the RT activity by about 90% at ambient temperature and 37° C. but the level of inhibition was 45% at 55° C. The significant reduction in the level of inhibition at 55° C. suggests that the hairpin structure was destabilized by the introduction of the two mismatches. This result suggests that "hot-start" of the polymerase reaction catalyzed by reverse transcriptases can be enhanced by using a nucleic acid inhibitor that forms double stranded at ambient temperature but denatures at the desired polymerization temperature.

Nucleic Acid Inhibitor H

Under the experimental conditions, complexing ThermoScript™ I with about 50-fold excess of this nucleic acid prior to initiating the polymerization reaction inhibition the RT activity by about 50% at ambient temperature. The level of inhibition at 37° C. and 55° C. was negligible, within our experimental error. This result suggests that there is a background level of inhibition at ambient temperature that is not derived from the primer/template substrate competition. Whereas the level of inhibition by the addition of inhibitor H was minimal at 37° C. and 55° C., under our experimental condition.

The relative polymerase activities of Thermoscript™ I in the absence and presence of the remaining nucleic acid inhibitors described above are shown in FIG. 6B. For each set of reaction conditions, the three bars from left to right denote reactions performed at ambient temperature, 37° C. and 55° C., respectively. TS, TS-C, TS-H, TS-E, TS-F and TS-G denote polymerase reaction initiated by Thermo-Script™ I, ThermoScript™ I-nucleic acid inhibitor C complex, ThermoScript™ I-nucleic acid inhibitor H complex, ThermoScript™ I-nucleic acid inhibitor E complex, ThermoScript™ I-nucleic acid inhibitor F complex, and ThermoScript™ I-nucleic acid inhibitor G complex, respectively.

Nucleic Acid Inhibitor C

Under the experimental conditions, complexing Thermo-Script™ I with about 50-fold excess of this nucleic acid (DNA/DNA) prior to initiating the polymerase inhibited the RT activity by about 70% at each of the reaction temperature. The relative similarity of the level of inhibition is indicative of the stability of the double stranded structure of this nucleic acid sequence in the temperature range in which the RT activity was assayed.

Nucleic Acid Inhibitor H

Under the experimental conditions, complexing Thermo-Script™ I with about 50-fold excess of this nucleic acid prior to initiating the polymerization reaction inhibited the RT activity by about 400/o at ambient temperature. The level of inhibition at 37° C. and 55° C. was negligible, within our experimental error.

Nucleic Acid Inhibitor E

Under the experimental conditions, complexing Thermo-Script™ I with about 50-fold excess of this nucleic acid prior to initiating the polymerization reaction inhibited the RT activity by more than 90% at ambient temperature and 37° C. but the level of inhibition was 60% at 55° C.

Nucleic Acid Inhibitor F

Under the experimental conditions, complexing Thermo-Script™ I with about 50-fold excess of this nucleic acid prior to initiating the polymerization reaction inhibited the RT activity by about 80% at ambient temperature, 65% at 37° C. and 40% at 55° C. The decrease in the level of inhibition in correlation to the increase of the reaction temperature is indicative of the destabilization of the hairpin structure due to the three mismatches.

Nucleic Acid Inhibitor G

Under the experimental conditions, complexing Thermo-Script™ I with about 50-fold excess of this nucleic acid prior to initiating the polymerization reaction inhibited the RT activity by about 80% at ambient temperature, 55% at 37° C. and 30% at 55° C. The decrease in the level of inhibition in correlation to the increase of the reaction temperature is indicative of the destabilization of the hairpin structure due to the three mismatches.

EXAMPLE 8

Inhibition of Reverse Transcriptase Activity within a Cell

The oligonucleotides of the present invention may be used to inhibit the activity of a revere transcriptase enzyme with a cell. Oligonucleotides for use inside a cell may optionally be modified to render them resistant to one or more nuclease enzymes that may be present in a cell. For example, a derivative of the nucleic acid inhibitor may be synthesized with one or more of the following modifications: 1) one or more of the ribose groups on the RNA portion of the oligonucleotide may be alkylated, for example, methylated, preferably at the 2'-OH to produce a 2'-O methyl; 2) one or more of the internucleotide linkages of the oligonucleotide, for example, in the DNA portion of the nucleic acid, may contain a modified linkage, for example, a phosphorothioate linkage; 3) the 3' terminus of the oligonucleotide may be capped so as to be non-extendable, for example, with a phosphate, phoshorothioate or a dideoxynucleotide or other modification of the 3'-hydroxyl so as to make it not extendable. Other modification that increase the level of resistance to cellular RNase activity and/or reduce the efficiency of DNA degradation by other cellular factors are known to those skilled in the art and may be incorporated into the design of the oligonucleotides of the present invention. In addition to rendering the oligonucleotides resistant to one or more cellular degradation factors, phosphorothioate reduces the possibility of homologous recombination into the host chromosome should a given inhibitor contain a region homologous to one on the host chromosome.

Oligonucleotides may be assayed to determine if they have an inhibitory effect on reverse transcriptase activity in a cell. Cells to be treated with the oligonucleotides of the invention, for example NIH3T3 cells may be transfected with the nucleic acid (Life Technologies, Inc.) using any method known to those skilled in the art. In some preferred embodiments, the oligonucleotides of the invention may be introduced into the cells using lipid mediated transfection (see, for example, U.S. Pat. Nos. 5,334,761; 5,674,908; 5,627,159; 5,736,392; 5,279,833 and published international application WO 94/27345 all of which are specifically incorporated herein by reference).

Following transfection of the cells, a virus expressing a reverse transcriptase (for example, Moloney Murine Leukemia V, M-MLV) may be added so as to efficiently infect cells with the virus and provide a source of reverse transcriptase activity. (Jolicoeur, P. and Rassart, E., 1980). An aliquot of the cells will be centrifuged and lysed at time intervals in order to assay for reverse transcriptase activity. Comparing the level of RT activity derived from cells that are transfected with a nucleic acid inhibitor and those that are not transfected, the efficacy of inhibition of viral proliferation in the cell can be determined.

EXAMPLE 9

Inhibition of Taq Polymerase Using Phosphorothioate Substituted Oligonucleotides In some preferred embodiments, one or more phosphorothioate residues may be incorporated into the oligonucleotides of the present invention. Those skilled in the art will appreciate that oligonucleotides incorporating such internucleotide linkages may be more resistant to nuclease activities that may be present in a reaction mixture or within a cell. Accordingly, such modifications may be made in oligonucleotides intended for in vivo or in vitro use. In some preferred embodiments, all of the internucleotide linkages may be phosphorotioate linkages.

In some embodiments, the 3'-terminus of an oligonucleotide of the invention may be modified to render the oligonucleotide more resistant to any 3'-to 5'-exonuclease activity present in a reaction mixture or within a cell. In some embodiments, the 3'-hydroxyl of the oligonucleotide may be modified, for example, by coupling a spacer modifier to the hydroxyl group. Such spacer modifiers are commercially available (Glen Research) and may comprise a chain of carbon atoms which may be substituted with one or more groups containing heteroatoms. In some preferred embodiments, the 3'-hydroxyl of the oligonucleotides of the invention may be modified with a 3 carbon spacer which terminates in a group containing a heteroatom such as, for example, an amine group or a hydroxyl group. The incorporation of such spacer modifiers into an oligonucleotide may be accomplished using chemistries well known to those skilled in the art for example, by the incorporation of a suitably blocked phophoramidite version of the spacer.

To examine the effectiveness of phosphorothioate modified oligonucleotides to inhibit Taq polymerase oligonucleotides were constructed in which all phosphate internucleotide linkages were change to phophorothioate internucleotide linkages. Four such oligonucleotides were constructed and their sequences are given below. HPHH1 is a phosphorothioate hairpin oligonucleotide with a 3 nucleotide loop, a melting temperature of the duplex region of 59° C. and a ΔG=−15.70 kcal/mol of formation of the duplex.

(SEQ ID NO:9)

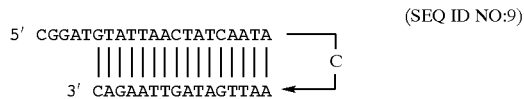

HPHH2 is a phosphorothioate hairpin oligonucleotide with a 3 nucleotide loop, a melting temperature of the duplex region of 67° C. and a ΔG=−18.10 kcal/mol of formation of the duplex.

(SEQ ID NO:10)

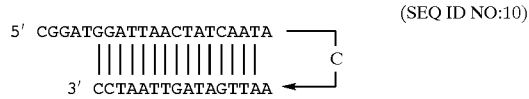

HPHH3 is a phosphorothioate hairpin oligonucleotide with a 5 nucleotide loop and a melting temperature of the duplex region of 70° C. and a ΔG=−18.90 kcal/mol of formation of the duplex.

(SEQ ID NO:11)

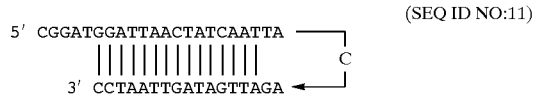

HPHH4 is a phosphorothioate oligonucleotide with a 4 nucleotide loop and a melting temperature of 65° C. of the duplex and a ΔG=−13.5 kcal/mol of formation of the duplex.

(SEQ ID NO:12)

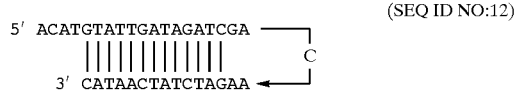

The bases involved in formation of the stem structure are indicated by a vertical line. When the oligonucleotide was modified at the 3'-terminal with a 3 carbon spacer group ending in a hydroxyl, the designation Sspa3 was added to the name of oligonucleotide.

Figure 7:
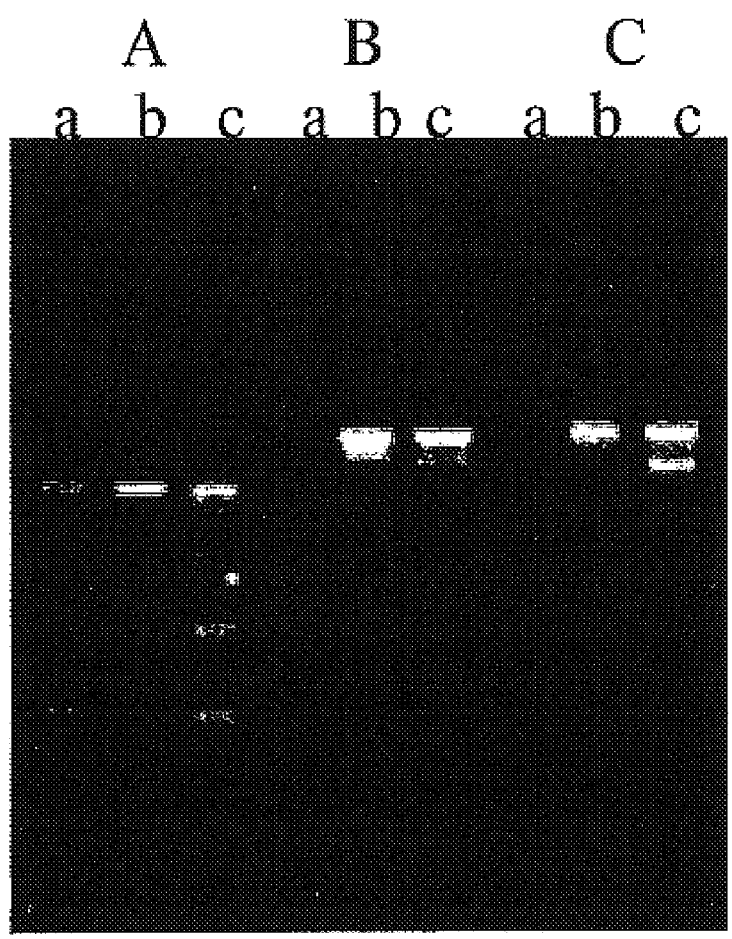
FIG. 7 is a photograph of an agarose gel showing the results of amplification reactions using a 1.6 kb (A), a 2 kb (B) and a 2.6 kb (C) fragment of the NF2 gene. In each panel, lane a is the amplification using Taq polymerase alone, lane b is the amplification reaction in the presence of inhibitor HPHH4Sspa3 at a molar ratio of 1.2:1 inhibitor: polymerase and lane c is the amplification using Platinum Taq.

With reference to FIG. 7, amplification reactions to produce a 1.6 kb (A), a 2 kb (B) and a 2.6 kb (C) fragment of the NF2 gene. In each panel, lane a is the amplification using Taq polymerase alone, lane b is the amplification reaction in the presence of inhibitor HPHH4Sspa3 at a molar ratio of 1.2:1 inhibitor: polymerase and lane c is the amplification using Platinum Taq. The template was 200 ng of genomic DNA. A comparison of lane b to lanes a and c in each panel shows that the presence of the inhibitor improves the amount of full length product and reduces the amount of shorter products under these reaction conditions.

Figure 8:
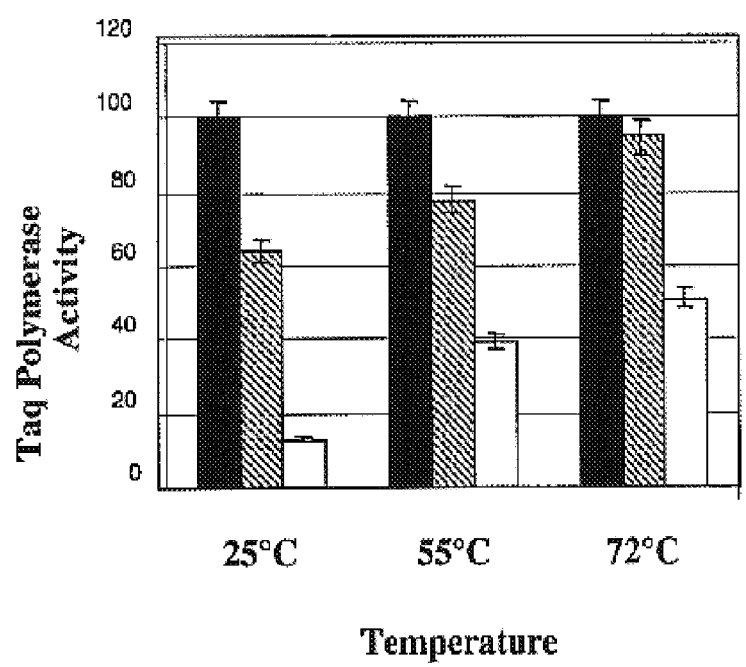
FIG. 8 is a bar graph showing the results of a dNTP incorporation assay at the indicated temperatures. At each temperature, the solid black rectangle reports the results obtained with Taq polymerase alone, the striped rectangle report the results obtained with inhibitor HPHH4Sspa3 at a molar ration of 2:1 inhibitor:polymerase, the white rectangle report the results obtained with the same inhibitor at a molar ratio of 7.5:1 inhibitor:polymerase.

As shown in FIG. 8, the activity of Taq polymerase in a nucleotide incorporation assay was determined at three temperatures (25° C., 55° C. and 72° C.) in the presence of two different concentrations of inhibitor HPHH4Sspa3 (molar ratios of 2:1 and 7.5:1 inhibitor:polymerase). At each temperature, the solid black bar is the Taq polymerase alone, the striped bar is Taq polymerase plus inhibitor at a 2:1 ratio of inhibitor to polymerase and the solid white bar is Taq plus inhibitor at a 7.5:1 ratio of inhibitor:polymerase. The incorporation was assayed in a PCR reaction mixture incubated at the indicated temperature in the presence of alpha-[$^{32}$P]-dCTP. After 30 minutes, the reactions were stopped by the addition of EDTA and an aliquot of each reaction was spotted onto GF/C filters. The filters were washed with TCA and counted. The activity was normalized to the amount of activity of the Taq polymerase at the same temperature.

At 25° C. and a 2:1 ratio, Taq activity was reduced to approximately 60% of the un-inhibited polymerase while a 7.5:1 ratio reduced activity by approximately 90%. At 55° C. (a typical annealing temperature) inhibition was still observed, approximately a 20% and 60% reduction in activity at 2:1 and 7.5:1 respectively. At 72° C. (a typical extension temperature) inhibition was nearly eliminated at a 2.5:1 ratio and was approximately 50% at a 7.5:1 ratio. These data indicate that the inhibition is temperature dependent with more inhibition observed at lower temperatures (i.e., when the oligonucleotide is in a hairpin structure) and less at a higher temperature.

Figure 9:
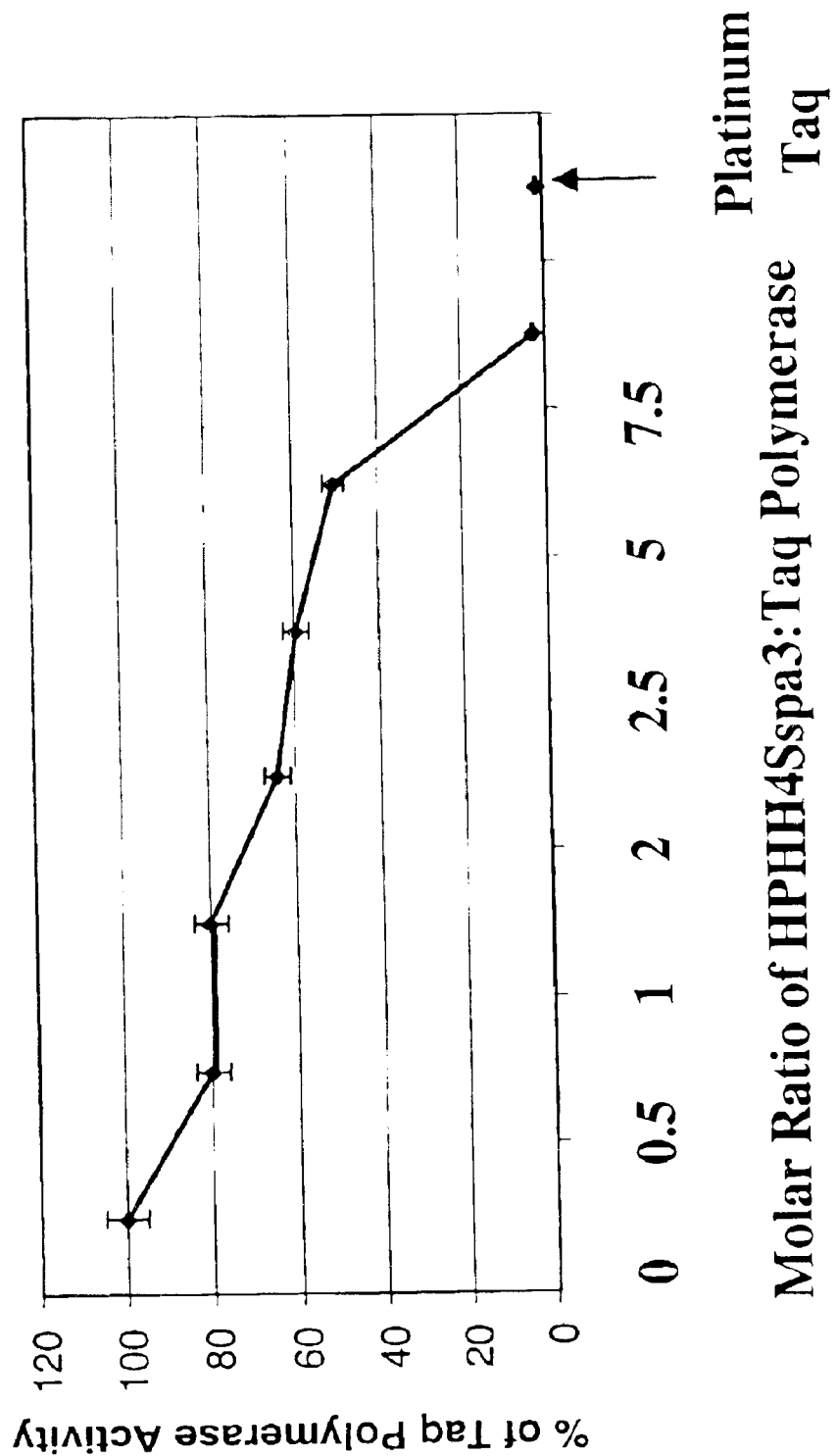
FIG. 9 is a graph showing the dose dependent inhibition of Taq polymerase by inhibitor present HPHH4Sspa3 present at the indicated molar ratios.

The concentration dependence of the inhibition of Taq polymerase by inhibitor HPHHSspa3 was studied at 37° C. and the results are shown in FIG. 9. The incorporation assay described above was used. These results indicate that the inhibition is dose dependent with a slight (20%) inhibition seen at a molar ration of 0.5:1 inhibitor: polymerase up to a nearly complete inhibition (96%) seen at 7.5:1. By way of comparison, a Taq polymerase inhibited by antibody (Platinum Taq) was tested under the same conditions. At a molar ratio of 7.5:1, the inhibitors of the present invention provide a comparable amount of inhibition of Taq activity as the antibody.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of preparing cDNA from mRNA, comprising:

mixing one or more mRNA templates with one or more reverse transcriptases, and with one or more double stranded inhibitory nucleic acids; and incubating said mixture under conditions sufficient to synthesize one or more cDNA molecules complementary to all or a portion of said templates.

2. The method of claim 1, wherein said mixing is accomplished under conditions sufficient to prevent nucleic acid synthesis and/or allow binding of said one or more double stranded inhibitory nucleic acids to said reverse transcriptase.

* * * * *

SEQUENCE LISTING

<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: nucleic
      acid inhibitor
<221> NAME/KEY: stem_loop
<222> LOCATION: (5)..(34)

<400> SEQUENCE: 1
cccaatatgg accggtcgaa agaccggtcc atat                             34

<210> SEQ ID NO 2
<211> LENGTH: 55
<212> TYPE: DNA
<213> ORGANISM: Artificial Sequence
<220> FEATURE:
<223> OTHER INFORMATION: Description of Artificial Sequence: nucleic
      acid inhibitor
<221> NAME/KEY: stem_loop
<222> LOCATION: (2)..(55)

<400> SEQUENCE: 2
ccatgcaggt agccgatgaa ctggtcgaaa gaccagttca tcggctacct gcatg       55

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: nucleic
      acid inhibitor
<221> NAME/KEY: stem_loop
<222> LOCATION: (11)..(44)

<400> SEQUENCE: 3
aattaatgta tatattatta ctataccggt atagtaataa tata                  44

<210> SEQ ID NO 4
<211> LENGTH: 50
<212> TYPE: DNA
<213> ORGANISM: Artificial Sequence
<220> FEATURE:
<223> OTHER INFORMATION: Description of Combined DNA/RNA Molecule: RNA
      bases from 1-25 and DNA bases from 26-50
<223> OTHER INFORMATION: Description of Artificial Sequence: nucleic
      acid inhibitor
<221> NAME/KEY: stem_loop
<222> LOCATION: (9)..(50)

<400> SEQUENCE: 4
aauuaaugua uauauuauua cuauaccgaa gggtatagta ataatatata             50

<210> SEQ ID NO 5
<211> LENGTH: 50
<212> TYPE: DNA
<213> ORGANISM: Artificial Sequence
<220> FEATURE:
<223> OTHER INFORMATION: Description of Combined DNA/RNA Molecule: RNA
      bases from 1 to 25 and DNA bases from 25-48
<223> OTHER INFORMATION: Description of Artificial Sequence: nucleic
      acid inhibitor
<221> NAME/KEY: stem_loop
<222> LOCATION: (9)..(50)

```
-continued

<400> SEQUENCE: 5
aauuaaugua uauauuauua cuauaccgaa gggtataata atagtatata          50

<210> SEQ ID NO 6
<211> LENGTH: 50
<212> TYPE: DNA
<213> ORGANISM: Artificial Sequence
<220> FEATURE:
<223> OTHER INFORMATION: Description of Combined DNA/RNA Molecule: RNA
      bases from 1-25 and DNA bases from 26-50
<223> OTHER INFORMATION: Description of Artificial Sequence: nucleic
      acid inhibitor
<221> NAME/KEY: stem_loop
<222> LOCATION: (9)..(50)

<400> SEQUENCE: 6
aauuaaugua uauauuauua cuauaccgaa gggtataatg agagtatata          50

<210> SEQ ID NO 7
<211> LENGTH: 50
<212> TYPE: DNA
<213> ORGANISM: Artificial Sequence
<220> FEATURE:
<223> OTHER INFORMATION: Description of Combined DNA/RNA Molecule: RNA
      bases from 1-25 and DNA bases from 26-50
<223> OTHER INFORMATION: Description of Artificial Sequence: nucleic
      acid inhibitor
<221> NAME/KEY: stem_loop
<222> LOCATION: (9)..(50)

<400> SEQUENCE: 7
aauuaaugua uauauuauua cuauaccgaa gggtataatg agagtatata          50

<210> SEQ ID NO 8
<211> LENGTH: 50
<212> TYPE: DNA
<213> ORGANISM: Artificial Sequence
<220> FEATURE:
<223> OTHER INFORMATION: Description of Combined DNA/RNA Molecule: RNA
      bases from 1-25 and DNA bases from 26-50
<223> OTHER INFORMATION: Description of Artificial Sequence: nucleic
      acid inhibitor

<400> SEQUENCE: 8
aauuaaugua uauauuauua cuauaccgaa aatatataat gatgatatag          50

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotides
<221> NAME/KEY: stem_loop
<222> LOCATION: (6)..(38)

<400> SEQUENCE: 9
cggatgtatt aactatcaat acaattgata gttaagac                       38

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotides
<221> NAME/KEY: stem_loop
<222> LOCATION: (6)..(38)
```

-continued

```
<400> SEQUENCE: 10
cggatggatt aactatcaat acaattgata gttaatcc                                38

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotides
<221> NAME/KEY: stem_loop
<222> LOCATION: (6)..(40)

<400> SEQUENCE: 11
cggatggatt aactatcaat tacagattga tagttaatcc                              40

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: synthetic
      oligonucleotides
<221> NAME/KEY: stem_loop
<222> LOCATION: (4)..(35)

<400> SEQUENCE: 12
acatgtattg atagatcgac aagatctatc aatac                                   35
```